(12) United States Patent
Pless et al.

(10) Patent No.: US 8,934,980 B2
(45) Date of Patent: Jan. 13, 2015

(54) DIFFERENTIAL NEUROSTIMULATION THERAPY DRIVEN BY PHYSIOLOGICAL THERAPY

(71) Applicant: NeuroPace, Inc., Mountain View, CA (US)

(72) Inventors: Benjamin D. Pless, Atherton, CA (US); Thomas K. Tcheng, Pleasant Hill, CA (US)

(73) Assignee: NeuroPace, Inc., Mountain VIew, CA (US)

( * ) Notice: Subject to any disclaimer, the term of this patent is extended or adjusted under 35 U.S.C. 154(b) by 67 days.

(21) Appl. No.: 13/784,569

(22) Filed: Mar. 4, 2013

(65) Prior Publication Data

US 2013/0184780 A1 Jul. 18, 2013

Related U.S. Application Data

(63) Continuation of application No. 13/523,855, filed on Jun. 14, 2012, now Pat. No. 8,423,145, which is a continuation of application No. 13/109,970, filed on May 17, 2011, now Pat. No. 8,224,452, which is a (Continued)

(51) Int. Cl.
*A61N 1/00* (2006.01)
*A61N 1/36* (2006.01)
(Continued)

(52) U.S. Cl.
CPC ....... *A61N 1/36135* (2013.01); *A61M 5/14276* (2013.01); *A61N 1/36064* (2013.01); *A61N 1/0529* (2013.01); *A61N 1/0531* (2013.01);
(Continued)

(58) Field of Classification Search
CPC .. A61B 5/0015; A61B 5/0031; A61B 5/0002; A61B 5/0006; A61B 5/04004; A61B 5/04012; A61B 5/04014; A61B 5/0476; A61B 5/048
USPC ......................................... 607/45, 32, 60, 59
See application file for complete search history.

(56) References Cited

U.S. PATENT DOCUMENTS 3,531,561 A 9/1970 Trehu
3,565,066 A 2/1971 Roaf et al.
(Continued)

FOREIGN PATENT DOCUMENTS

DE 8528003 2/1986
DE 8706912 10/1987
(Continued)

OTHER PUBLICATIONS

Adriano, K.P. et al., (1994). "Processing and Characterization of Absorbable Polyactide Polymers for Use in Surgical Implants," Journal of Applied Biomaterials 5: 133-140.
(Continued)

*Primary Examiner* — Scott Getzow
(74) *Attorney, Agent, or Firm* — Arent Fox LLP

(57) ABSTRACT

An implantable neurostimulator system adapted to provide therapy for various neurological disorders is capable of varying therapy delivery strategies based on the context, physiological or otherwise, into which the therapy is to be delivered. Responsive and scheduled therapies can be varied depending on various sensor measurements, calculations, inferences, and device states (including elapsed times and times of day) to deliver an appropriate course of therapy under the circumstances.

15 Claims, 11 Drawing Sheets

Related U.S. Application Data continuation of application No. 11/436,191, filed on May 16, 2006, now Pat. No. 7,966,073, which is a continuation of application No. 10/121,933, filed on Apr. 12, 2002, now abandoned, which is a continuation-in-part of application No. 09/962,940, filed on Sep. 24, 2001, now Pat. No. 6,480,743, which is a continuation-in-part of application No. 09/543,264, filed on Apr. 5, 2000, now Pat. No. 6,944,501, and a continuation-in-part of application No. 09/543,450, filed on Apr. 5, 2000, now Pat. No. 6,466,822.

(51) Int. Cl.
  *A61M 5/142* (2006.01)
  *A61N 1/05* (2006.01)

(52) U.S. Cl.
  CPC .......... *A61N1/0539* (2013.01); *A61N 1/36067* (2013.01); *A61N 1/36078* (2013.01)
  USPC .......................................................... 607/45

(56) References Cited

U.S. PATENT DOCUMENTS

| | | |
|---|---|---|
| 3,636,956 A | 1/1972 | Schneider |
| 3,850,161 A | 11/1974 | Liss |
| 3,960,151 A | 6/1976 | Kuhn |
| 3,993,046 A | 11/1976 | Fernandez et al. |
| 4,429,690 A | 2/1984 | Angelino-Pievani |
| 4,523,591 A | 6/1985 | Kaplan et al. |
| 4,566,464 A | 1/1986 | Piccone et al. |
| 4,702,254 A | 10/1987 | Zabara |
| 4,781,183 A | 11/1988 | Casey et al. |
| 4,800,895 A * | 1/1989 | Moberg et al. ................ 600/544 |
| 4,867,164 A | 9/1989 | Zabara |
| 4,905,680 A | 3/1990 | Tunc |
| 4,979,511 A | 12/1990 | Terry |
| 5,025,807 A | 6/1991 | Zabara |
| 5,029,590 A * | 7/1991 | Allain et al. ................ 600/523 |
| 5,031,618 A | 7/1991 | Mullett |
| 5,047,930 A * | 9/1991 | Martens et al. ............... 600/301 |
| 5,129,903 A | 7/1992 | Luhr et al. |
| 5,154,172 A | 10/1992 | Terry et al. |
| 5,179,950 A | 1/1993 | Stanislaw |
| 5,186,170 A | 2/1993 | Varrichio et al. |
| 5,188,104 A | 2/1993 | Wernicke et al. |
| 5,205,285 A | 4/1993 | Baker |
| 5,215,086 A | 6/1993 | Terry et al. |
| 5,215,089 A | 6/1993 | Baker |
| 5,222,494 A | 6/1993 | Baker |
| 5,231,988 A | 8/1993 | Wernicke et al. |
| 5,235,980 A | 8/1993 | Varrichio et al. |
| 5,237,991 A | 8/1993 | Baker et al. |
| 5,251,634 A | 10/1993 | Weinberg |
| 5,263,480 A | 11/1993 | Wernicke et al. |
| 5,269,303 A | 12/1993 | Wernicke et al. |
| 5,293,879 A | 3/1994 | Vonk et al. |
| 5,299,569 A | 4/1994 | Wernicke et al. |
| 5,304,206 A | 4/1994 | Baker et al. |
| 5,311,876 A | 5/1994 | Olsen et al. |
| 5,330,515 A | 7/1994 | Rutecki et al. |
| 5,335,657 A | 8/1994 | Terry et al. |
| 5,349,962 A | 9/1994 | Lockard et al. |
| 5,351,394 A | 10/1994 | Weinberg |
| 5,372,598 A | 12/1994 | Luhr et al. |
| 5,413,577 A | 5/1995 | Pollock |
| 5,413,594 A * | 5/1995 | Williams ..................... 607/32 |
| 5,474,547 A | 12/1995 | Aebischer et al. |
| 5,522,863 A | 6/1996 | Spano et al. |
| 5,531,778 A | 7/1996 | Maschino et al. |
| 5,540,730 A | 7/1996 | Terry et al. |
| 5,540,734 A | 7/1996 | Zabara |
| 5,569,250 A | 10/1996 | Sarver et al. |
| 5,571,150 A | 11/1996 | Wernicke et al. |
| 5,604,204 A | 2/1997 | Ammann et al. |
| 5,676,655 A | 10/1997 | Howard et al. |
| 5,683,422 A | 11/1997 | Rise |
| 5,707,396 A | 1/1998 | Benabid |
| 5,707,400 A | 1/1998 | Terry et al. |
| 5,711,316 A | 1/1998 | Elsberry et al. |
| 5,713,923 A | 2/1998 | Ward et al. |
| 5,716,377 A | 2/1998 | Rise et al. |
| 5,735,814 A | 4/1998 | Elsberry et al. |
| 5,752,979 A | 5/1998 | Benabid |
| 5,792,186 A | 8/1998 | Rise |
| 5,792,212 A | 8/1998 | Weijand |
| 5,800,474 A | 9/1998 | Benabid et al. |
| 5,832,932 A | 11/1998 | Elsberry et al. |
| 5,833,709 A | 11/1998 | Rise et al. |
| 5,868,746 A | 2/1999 | Sarver et al. |
| 5,871,506 A | 2/1999 | Mower |
| 5,928,272 A | 7/1999 | Adkins et al. |
| 5,938,689 A | 8/1999 | Fischell et al. |
| 5,978,702 A | 11/1999 | Ward et al. |
| 5,995,868 A * | 11/1999 | Dorfmeister et al. ......... 600/544 |
| 6,006,124 A | 12/1999 | Fischell et al. |
| 6,016,449 A | 1/2000 | Fischell et al. |
| 6,018,682 A | 1/2000 | Rise |
| 6,024,702 A | 2/2000 | Iversen |
| 6,066,163 A | 5/2000 | John |
| 6,095,148 A | 8/2000 | Shastri et al. |
| 6,161,045 A | 12/2000 | Fischell et al. |
| 6,366,813 B1 | 4/2002 | DiLorenzo |
| 6,466,822 B1 | 10/2002 | Pless |
| 6,480,743 B1 | 11/2002 | Kirkpatrick et al. |
| 6,597,954 B1 | 7/2003 | Pless et al. |
| 6,665,562 B2 | 12/2003 | Gluckman et al. |
| 6,738,671 B2 * | 5/2004 | Christophersom et al. ..... 607/60 |
| 6,810,285 B2 | 10/2004 | Pless et al. |
| 6,819,956 B2 | 11/2004 | DiLorenzo |
| 7,089,059 B1 | 8/2006 | Pless |
| 7,209,787 B2 | 4/2007 | DiLorenzo |
| 7,231,254 B2 | 6/2007 | DiLorenzo |
| 7,242,984 B2 | 7/2007 | DiLorenzo |
| 7,277,758 B2 | 10/2007 | DiLorenzo |
| 7,324,851 B1 | 1/2008 | DiLorenzo |
| 7,403,820 B2 | 7/2008 | DiLorenzo |
| 7,529,582 B1 | 5/2009 | DiLorenzo |
| 7,599,736 B2 | 10/2009 | DiLorenzo |
| 7,630,757 B2 | 12/2009 | Dorfmeister et al. |
| 7,747,325 B2 | 6/2010 | Dilorenzo |
| 7,853,329 B2 | 12/2010 | DiLorenzo |
| 7,930,035 B2 | 4/2011 | DiLorenzo |
| 7,966,073 B2 | 6/2011 | Pless et al. |
| 7,974,696 B1 | 7/2011 | DiLorenzo |
| 2007/0161919 A1 | 7/2007 | DiLorenzo |

FOREIGN PATENT DOCUMENTS

| | | |
|---|---|---|
| DE | 3701765 | 6/1988 |
| DE | 4028021 | 5/1991 |
| EP | 0195455 | 9/1986 |
| EP | 0276153 | 7/1988 |
| EP | 0290138 | 11/1988 |
| EP | 0291632 | 11/1988 |
| EP | 0347658 | 12/1989 |
| EP | 0491983 | 7/1992 |
| EP | 0911061 | 4/1999 |
| GB | 2140523 | 11/1984 |
| GB | 0433852 | 3/1996 |

OTHER PUBLICATIONS

Cooper, I.S. et al., (1974). "The Effect of Chronic Stimulation of Cerebellar Cortex on Epilepsy in Man," In The Cerebellum, Epilepsy, and Behavior. Cooper, I.S. et al., eds., Plenum Press:New York, pp. 119-171.

Cooper, I.S. et al., (1977/1978). "Safety and Efficacy of Chronic Cerebellar Stimulation," Appl. Neurophysiol. 40:124-134.

Cooper, I.S. and Upton, A.R.M. (1978). "Effects of Cerebellar Stimulation on Epilepsy, the EEG and Cerebral Palsy in Man," In Contemporary Clinical Neurophysiology (EEG Suppl. No. 34). Cobb, W.A.

(56) References Cited

OTHER PUBLICATIONS et al., eds., Elsevier Scientific Publishing: Amsterdam, pp. 349-354.
Davis, R. and Emmonds, S.E. (1992). "Cerebellar Stimulation for Seizure Control: 17-Year Study," Stereotact. Funct. Neurosurg. 58:200-208.
Lee, S.A. et al., "Intracranial EEG Seizure-Onset Patterns in Neocortical Epilepsy", Epilepsia, 2000, 41 (3): 297-307.
Lesser, R.P. et al., "Brief Bursts of Pulse Stimulation Terminate Afterdischarges Caused by Cortical Stimulation", Neurologogy 1999; 53 (Dec.): 2073-81.
Schiller, Y et al., "Characterization and Comparison of Local Onset and Remote Propagated Electrographic Seizures Recorded with Intracranial Electrodes", Epilepsia, 1998; 39(4): 380-88.
Chkhenkeli, S.A. and, Chkhenkeli, I.S. et al., (1997). "Effects of Therapeutic Stimulation of Nucleus Caudatus on Epileptic Electrical Activity of Brain in Patents with Intractable Epilepsy," Stereotact Funct Neurosurg 69:221-224.
U.S. Appl. No. 60/562,487, filed Apr. 14, 2004.
U.S. Appl. No. 60/460,140, filed Apr. 3, 2003.
U.S. Appl. No. 60/438,286, filed Jan. 6, 2003.
U.S. Appl. No. 60/436,792, filed Dec. 27, 2002.
U.S. Appl. No. 60/427,699, filed Nov. 20, 2002.
U.S. Appl. No. 60/095,413, filed Aug. 5, 1998.
Second Examination Report for European Application No. 01303246.1 (corresponding to U.S. Appl. No. 09/543,450) (Mar. 9, 2007).
Response to First Examination Report for European Application No. 01303246.1 (corresponding to U.S. Appl. No. 09/543,450) (Apr. 13, 2006).
First Examination Report for European Application No. 01303246.1 (corresponding to U.S. Appl. No. 09/543,450)(Oct. 18, 2005).
European Search Report for European Application No. 01303246.1 (corresponding to U.S. Appl. No. 09/543,450) (Mar. 1, 2004).
Second Examination Report for European Application No. 01303245.3 (corresponding to U.S. Appl. No. 09/543,264) (Mar. 9, 2007).
Response to First Examination Report for European Application No. 01303245.3 (corresponding to U.S. Appl. No. 09/543,264 (Apr. 20, 2006).
Velasco, F. et al., (1995). "Electrical Stimulation of the Centromedian Thalamic Nucleus in Control of Seizures: Long Term Studies," Epilepsia 36(1):63-71.
Thaller, S.R. et al., (1992). "Use of Biodegradable Plates and Screws in a Rabbit Model," Journal of Craniofacial Surgery 2(4):168-173.
Schiff, S. et al., (1994). "Controlling Chaos in the Brain," Nature 370:615-620.
Sayler, K.E. et al., (1994). "A Comparative Study of the Effects of Biodegradable and Titanium Plating Systems on Cranial Growth and Structure: Experimental Study in Beagles," Plastic and Reconstructive Surgery 93(4):705-713.
Qu, H. and Gotman, J. (1995). "A Seizure Warning System for Long-Term Epilepsy Monitoring," Neurology 45:2250-2254.
Osario, I. et al., (1995). "A Method for Accurate Automated Real-Time Seizure Detection," Epilepsia, 36(supplement 4):4, Abstract No. 1.04.
Gotman, J. (1999). "Automatic Detection of Seizures and Spikes," Journal of Clinical Neurophysiology 16(2): 130-140.
Gerlach, K.L. (1993). "In-vivo and Clinical Evaluations of Poly(L-lactide) Plates and Screws for Use in Maxillofacial Traumatology," Clinical Materials 13:21-28.
Eppley, B.L. and Sadove, A.M. (1992). "Effects of Resorbable Fixation on Craniofacial Skeletal Growth: A Pilot Experimental Study," Journal of Craniofacial Surgery 3(4):190-196.
Response to First Examination Report for European Application No. 01303245.3 (corresponding to U.S. Appl. No. 09/543,264) (Apr. 20, 2006).
First Examination Report for European Application No. 01303245.3 (corresponding to U.S. Appl. No. 09/543,264) (Oct. 14, 2005).
European Search Report for European Application No. 01303245.3 (corresponding to U.S. Appl. No. 09/543,264) (Mar. 8, 2004).
Wagner, H.R. et al., "Suppression of Cortical Epileptiform Activity by Generalized and Localized ECoG Desynchronization", Electroencephalogr. Clin. Neurophysiol. 1975; 39(5).
Spencer, S.S. et al., "Morphological Patterns of Seizures Recorded Intracranially", Epilepsia, 1992,33(3): 537-45.
Limousin, P. "Multicentre European Study of Thalamic Stimulation in Parkinsonian and Essential Tremor", J. Neurol. Neurosurg. Psychiatry 1999; 66: 289-296 (Medtronic Activa).
Morris III, G.L. et al., "Long Term Treatment with Vagal Nerve Stimulation in Patients with Refractory Epilepsy," Neurology (Nov. 1999); 53(7): 1731-38 (Cyberonics NCP).

\* cited by examiner

DIFFERENTIAL NEUROSTIMULATION THERAPY DRIVEN BY PHYSIOLOGICAL THERAPY

CROSS-REFERENCE TO RELATED APPLICATIONS

This is a continuation application of and claims the benefit of U.S. patent application Ser. No. 13/523,855, now U.S. Pat. No. 8,423,145, filed on Jun. 14, 2012, entitled "Differential Neurostimulation Therapy Driven By Physiological Therapy" by Pless et al., which is a continuation application of and claims the benefit of U.S. patent application Ser. No. 13/109,970, now U.S. Pat. No. 8,224,452, filed on May 17, 2011, which is a continuation of and claims the benefit of U.S. patent application Ser. No. 11/436,191, now U.S. Pat. No. 7,966,073, filed on May 16, 2006, which is a continuation of and claims the benefit of U.S. Ser. No. 10/121,933 filed on Apr. 12, 2002, now abandoned, which is a continuation-in-part of and claims the benefit of U.S. patent application Ser. No. 09/962,940, now U.S. Pat. No. 6,480,743, filed on Sep. 24, 2001, which in turn is a continuation-in-part of and claims the benefit of U.S. patent application Ser. No. 09/543,264 filed on Apr. 5, 2000, now U.S. Pat. No. 6,944,501, and is also a continuation-in-part of and claims the benefit of U.S. patent application Ser. No. 09/543,450 also filed on Apr. 5, 2000, now U.S. Pat. No. 6,466,822, which are all incorporated herein by reference in their entirety. All of the aforementioned applications and/or patents are assigned to the assignee of the present application

FIELD

The disclosed embodiments relate to electrical stimulation therapy for neurological disorders, and more particularly to applying different types of therapy to treat different types of neurological events.

BACKGROUND

Epilepsy, a neurological disorder characterized by the occurrence of seizures (specifically episodic impairment or loss of consciousness, abnormal motor phenomena, psychic or sensory disturbances, or the perturbation of the autonomic nervous system), is debilitating to a great number of people. It is believed that as many as two to four million Americans may suffer from various forms of epilepsy. Research has found that its prevalence may be even greater worldwide, particularly in less economically developed nations, suggesting that the worldwide figure for epilepsy sufferers may be in excess of one hundred million.

Because epilepsy is characterized by seizures, its sufferers are frequently limited in the kinds of activities they may participate in. Epilepsy can prevent people from driving, working, or otherwise participating in much of what society has to offer. Some epilepsy sufferers have serious seizures so frequently that they are effectively incapacitated.

Furthermore, epilepsy is often progressive and can be associated with degenerative disorders and conditions. Over time, epileptic seizures often become more frequent and more serious, and in particularly severe cases, are likely to lead to deterioration of other brain functions (including cognitive function) as well as physical impairments.

The current state of the art in treating neurological disorders, particularly epilepsy, typically involves drug therapy and surgery. The first approach is usually drug therapy.

A number of drugs are approved and available for treating epilepsy, such as sodium valproate, phenobarbital/primidone, ethosuximide, gabapentin, phenytoin, and carbamazepine, as well as a number of others. Unfortunately, those drugs typically have serious side effects, especially toxicity, and it is extremely important in most cases to maintain a precise therapeutic serum level to avoid breakthrough seizures (if the dosage is too low) or toxic effects (if the dosage is too high). The need for patient discipline is high, especially when a patient's drug regimen causes unpleasant side effects the patient may wish to avoid.

Moreover, while many patients respond well to drug therapy alone, a significant number (at least 20-30%) do not. For those patients, surgery is presently the best-established and most viable alternative course of treatment.

Currently practiced surgical approaches include radical surgical resection such as hemispherectomy, corticectomy, lobectomy and partial lobectomy, and less-radical lesionectomy, transection, and stereotactic ablation. Besides being less than fully successful, these surgical approaches generally have a high risk of complications, and can often result in damage to eloquent (i.e., functionally important) brain regions and the consequent long-term impairment of various cognitive and other neurological functions. Furthermore, for a variety of reasons, such surgical treatments are contraindicated in a substantial number of patients. And unfortunately, even after radical brain surgery, many epilepsy patients are still not seizure-free.

Electrical stimulation is an emerging therapy for treating epilepsy. However, currently approved and available electrical stimulation devices apply continuous electrical stimulation to neural tissue surrounding or near implanted electrodes, and do not perform any detection—they are not responsive to relevant neurological conditions.

The NeuroCybernetic Prosthesis (NCP) from Cyberonics, for example, applies continuous electrical stimulation to the patient's vagus nerve. This approach has been found to reduce seizures by about 50% in about 50% of patients. Unfortunately, a much greater reduction in the incidence of seizures is needed to provide clinical benefit. The Activa device from Medtronic is a pectorally implanted continuous deep brain stimulator intended primarily to treat Parkinson's disease; it has also been tested for epilepsy. In operation, it supplies a continuous electrical pulse stream to a selected deep brain structure where an electrode has been implanted.

Continuous stimulation of deep brain structures for the treatment of epilepsy has not met with consistent success. To be effective in terminating seizures, it is believed that one effective site where stimulation should be performed is near the focus of the epileptogenic region of the brain. The focus is often in the neocortex, where continuous stimulation may cause significant neurological deficit with clinical symptoms including loss of speech, sensory disorders; or involuntary motion. Accordingly, research has been directed toward automatic responsive epilepsy treatment based on a detection of imminent seizure.

The episodic attacks or seizures experienced by a typical epilepsy patient are characterized by periods of abnormal neurological activity. "Epileptiform" activity refers to specific neurological activity associated with epilepsy as well as with an epileptic seizure and its precursors; such activity is frequently manifested in electrographic signals in the patient's brain.

Most prior work on the detection and responsive treatment of seizures via electrical stimulation has focused on analysis of electroencephalogram (EEG) and electrocorticogram (ECoG) waveforms. In general, EEG signals represent aggregate neuronal activity potentials detectable via electrodes applied to a patient's scalp, and ECoGs use internal electrodes near the surface of or within the brain. ECoG signals, deep-brain counterparts to EEG signals, are detectable via electrodes implanted on the dura mater, under the dura mater, or via depth electrodes (and the like) within the patient's brain. Unless the context clearly and expressly indicates otherwise, the term "EEG" shall be used generically herein to refer to both EEG and ECoG signals.

It is generally preferable to be able to detect and treat a seizure at or near its beginning, or even before it begins. The beginning of a seizure is referred to herein as an "onset." However, it is important to note that there are two general varieties of seizure onsets. A "clinical onset" represents the beginning of a seizure as manifested through observable clinical symptoms, such as involuntary muscle movements or neurophysiological effects such as lack of responsiveness. An "electrographic onset" refers to the beginning of detectable electrographic activity indicative of a seizure. An electrographic onset will frequently occur before the corresponding clinical onset, enabling intervention before the patient suffers symptoms, but that is not always the case. In addition, there often are perceptible changes in the EEG, or "precursors," that occur seconds or even minutes before the electrographic onset that can be identified and used to facilitate intervention before electrographic or clinical onsets occur. This capability would be considered seizure prediction, in contrast to the detection of a seizure or its onset.

It has been suggested that it is possible to treat and terminate seizures by applying specific responsive electrical stimulation signals to the brain. See, e.g., U.S. Pat. No. 6,016,449 to Fischel) et al., H. R. Wagner, et al., Suppression of Cortical Epileptiform Activity by Generalized and Localized ECoG Desynchronization, Electroencephalogr. Clin. Neurophysiol. 1975; 39(5): 499-506; and R. P. Lesser et al., Brief Bursts of Pulse Stimulation Terminate Afterdischarges Caused by Cortical Stimulation, Neurology 1999; 53(December): 2073-81. Unlike the continuous stimulation approaches, described above, responsive stimulation is intended to be performed only when a seizure (or other undesired neurological event) is occurring or about to occur. This approach is believed to be preferable to continuous or semi-continuous stimulation, as stimulation at inappropriate times and quantities may) result in the initiation of seizures, an increased susceptibility to seizures, or other undesired side effects. Responsive stimulation, on the other hand, tends to avoid side effects, to avoid undesired habituating and conditioning (learning) effects on the brain, and to prolong the battery life of an implantable device.

While responsive stimulation alone is considered an advantageous therapy for seizures, it is believed possible to further reduce the incidence of seizures by applying continuous or periodic scheduled stimulation to certain parts of the brain while also performing responsive electrical stimulation as described above. See, for example, U.S. patent application Ser. No. 09/543,450 filed on Apr. 5, 2000; U.S. Pat. No. 5,683,422 to Rise; and I. S. Cooper et al., "Effects of Cerebellar Stimulation on Epilepsy, the EEG and Cerebral. Palsy in Man," Electroencephalogr. Clin. Neurophysiol. 1978; 34: 349-54. Drug therapy, either continuous or applied by an implantable device upon demand or on a schedule, is also believed to be a useful adjunct to responsive and programmed electrical stimulation.

Current approaches to responsive stimulation have certain obvious drawbacks. In general, the need to apply responsive therapy indicates that a seizure or other event is imminent or already occurring, which might have adverse implications for the patient. Accordingly, it would be preferable to be able to detect events and conditions that precede seizures and treat them less aggressively, thereby discouraging the seizure from ever occurring.

Moreover, seizures (and other events) and their onsets almost always differ in some way—with different types, locations, and characteristics in different individuals, and also frequently between multiple events in the same individual. Finally, it should be recognized that certain treatments, and specifically certain kinds of stimulation might not work well for all of a patient's seizures, and in some cases, might even exacerbate some seizures. A Boolean responsive treatment strategy (i.e., a choice between applying one kind of therapy and not applying therapy at all) may not be effective in certain patients, and does not provide much of a structured course of treatment for episodes of varying severity.

Accordingly, and for the reasons set forth above, it is desirable to be able to apply the best possible therapy for each of a patient's episodes of epileptiform activity or other symptoms. Such therapy would have an increased chance of disrupting epileptiform activity, thereby avoiding, terminating, or lessening the severity of the patient's seizure disorder.

SUMMARY

The disadvantages of traditional and known approaches to electrical stimulation for epilepsy, including certain approaches to responsive stimulation, are ameliorated by the embodiments described herein. Generally, the disclosed embodiments provide responsive therapy for epilepsy and other neurological disorders, namely, therapy that is responsive to detected electrographic patterns, electrophysiological conditions, and other physiological conditions capable of being observed and identified through implanted sensors.

Various embodiments are capable of providing differential therapy based on a detected event type or other neurological or physiological context, thereby providing certain advantages over basic electrical neurostimulation therapy and responsive neurostimulation in general.

The different types of therapies deliverable by a system according to some embodiments can be based upon any of a number of different factors, including the type of onset, seizure, or other event detected; the location of the onset, seizure, or other event detected; the morphology or frequency content of the ECoG during the onset, seizure, or other event detected; whether the seizure or other event has generalized or propagated through the patient's brain; whether the patient is asleep or awake; and any other possible relevant electrophysiological or other characteristic (e.g., observed via an implanted sensor) of the patient, considered alone or in combination with detected events described above. Differing treatment approaches might also be affected by a state of the system (and in particular, the implantable device), and whether other treatments have recently been applied or are about to be applied.

The various treatment approaches offered by a system according to the disclosed embodiments are effective to avoid or stop an onset of a seizure or other neurological event, to halt the propagation of an existing seizure or neurological event, to reduce the susceptibility of a patient to seizures or other undesired symptoms or effects, or to warn a patient, caregiver, or physician of the patient's condition. These strategies and others will be apparent in connection with the detailed description set forth below.

Various different electrical stimulation approaches are possible. For example, and as treated in detail in U.S. Pat. No. 6,016,449 to Fischel) et al. and elsewhere, responsive stimulation can be applied at or near the focus of epileptiform activity. It may also be efficacious in certain circumstances to apply stimulation to a functionally relevant brain structure, either on a patient-specific basis (e.g., structures and pathways in communication with a seizure focus, lesion site, or other feature of interest, as described in U.S. patent application Ser. No. 09/724,805, filed on Nov. 28, 2000, which is hereby incorporated by reference as though set forth in full herein) or at a predetermined site known or suspected to have a role (e.g., the caudate nucleus, described in greater detail below). There are, of course, other possibilities that will be apparent to a practitioner of ordinary skill in the art.

Alternative therapies are also possible and are usable in various embodiments, including on-demand drug dispensing; audio, sensory, and somatosensory stimulation; and other approaches.

It will be appreciated that contextual information observed at the time of a neurological event of interest can be used in at least two ways. In connection with the embodiments described herein, such information can be used to determine the nature of the neurological event and hence what type of therapy (and how and where delivered) would be most effective. It is also possible to use information to provide adaptive therapy variations, in the manner described in U.S. patent application Ser. No. 09/962,940, of which the present disclosure is a continuation-in-part. The two approaches are not mutually exclusive, and as described below, can be used together.

Accordingly, a system in some embodiments generally includes an implantable neurostimulator capable of interfacing with external equipment, a detection subsystem capable of detecting a neurological event of interest in the patient and measuring or otherwise observing some characteristic of the neurological event, and a therapy subsystem capable of treating the patient by varying its treatment approach based on the observed characteristic. As used herein, the term therapy applies not only to a treatment intended to treat an emergent condition, but also to a prophylactic treatment intended to reduce the likelihood of a condition occurring.

Generally, various embodiments may be performed by measuring a characteristic of a detected neurological event, as described above, transforming or modifying a parameter associated with the characteristic, and using the parameter to select and transform a desired therapy that is deemed appropriate and effective given the nature of the event.

BRIEF DESCRIPTION OF THE DRAWINGS

These and other objects, features, and advantages will become apparent from the detailed description below and the accompanying drawings, in which.

DETAILED DESCRIPTION

Figure 1:
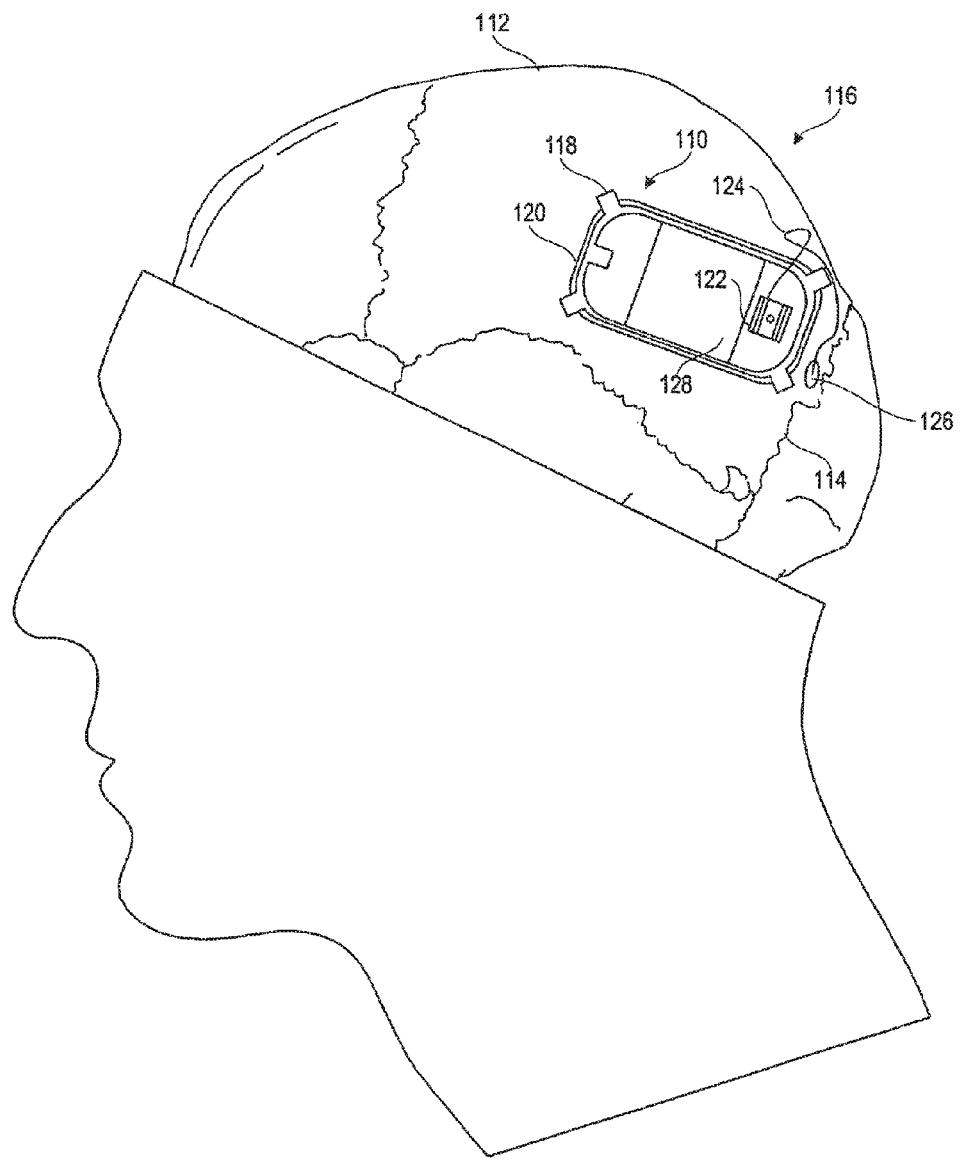
FIG. 1 is a schematic illustration of a patient's cranium showing the placement of an implantable neurostimulator according to an embodiment, including leads extending to the patient's brain.

Various embodiments are described below, with reference to detailed illustrative embodiments. It will be apparent that a system according to the invention may be embodied in a wide variety of forms. Consequently, the specific structural and functional details disclosed herein are representative and do not limit the scope of the invention.

In various embodiments, differential therapy is provided, that is, treatments that are tailored to the types and characteristics of seizures and other neurological events experienced by patients. This is accomplished by measuring or otherwise observing a characteristic of the event—typically the nature of a seizure onset, including its type, morphology, location, or other properties—and selecting and delivering a course of therapy accordingly. In addition, some embodiments use differential therapy applied prophylactically whereby treatments are tailored to characteristics of predictive events that generally precede neurological events, and where applying such tailored treatments is intended to reduce the likelihood of the neurological event occurring.

A determination as to what type of therapy to apply can be based upon many possible measurements and observations, several of which will be described in detail below (though other possibilities will be apparent to those of skill in the art of treating epilepsy and other neurological disorders with electrical stimulation and other therapies). In particular, various parameters can be measured at the time of a detected event, or before or after the event. In some embodiments, the systems and methods are not limited to single measurements, as trends and historical changes in neurological conditions, including (for purposes of illustration) but not limited to EEG activity, electrophysiological conditions, and neurotransmitter levels, can be observed and might, in some embodiments, guide treatment.

One neurological event characteristic that is particularly relevant to treatment is the type of seizure onset experienced by a patient. It has been found that single patients can experience multiple types of seizures at different times, and also that certain types of seizure onsets respond well to certain types of therapies, and that other types of onsets do not.

For a general description of several different onset types, see, e.g., S. Spencer et al., "Morphological Patterns of Seizures Recorded Intracranially," Epilepsia, 33(3): 537-45 (1992); and S.-A. Lee et al., "Intracranial EEG Seizure-Onset Patterns in Neocortical Epilepsy," Epilepsia, 41(3): 297-307 (2000).

Seizure onset types can often be characterized at least in part by their EEG morphologies. In particular, and by way of example, two common seizure onset types are characterized by distinctly different EEG patterns. A first type of seizure onset is defined by and includes quasi-sinusoidal, or relatively rounded, EEG waveforms. It has been found that such quasi-sinusoidal seizure onsets respond well to bursts of electrical pulses applied at or near the focus of the activity. A second type of seizure onset is defined by sharp, spiky EEG waveforms. Such onsets often do not respond well to bursts of electrical pulses, and alternative therapy approaches (such as relatively low-frequency sinusoidal stimulation) might be more effective.

There are other possible onset types; they may or may not be responsive to the types of therapy outlined above. For example, different onset types might also be defined by the presence or absence of a "beta buzz" (regular rhythmic activity generally in the 13-20 Hz range), whether EEG level suppression has occurred, or the presence of specific high- or low-frequency content in pre-onset electrographic measurements. As will be shown below, the embodiments described herein are flexible enough to measure, identify, and thereafter effectively treat nearly any kind of characteristic or stereotypical brain activity that can be clinically observed in EEG, electrophysiological conditions, or nearly any other measurable signal or quantity.

The location of a seizure onset can also provide useful information for a system according to some embodiments. For example, whether a seizure onset occurs in the temporal lobe or extra-temporally might prompt different treatment approaches. Also, it may be clinically relevant whether a detected seizure or its onset has occurred locally (i.e., near the detecting electrodes) or remotely (activity somewhere else in the brain that has propagated). It may be possible in some circumstances to differentiate local epileptiform and remote propagated activity based on observed electrographic activity. See, e.g., Y. Schiller et al., "Characterization and Comparison of Local Onset and Remote Propagated Electrographic Seizures Recorded with Intracranial Electrodes," Epilepsia, 39(4): 380-88 (1998) (examining local and remote electrographic patterns relating to both mesiotemporal and neocortical seizure onsets). In particular, rhythmic rounded theta-delta (up to about 7.5 Hz) waveforms are generally associated with propagated activity.

Whether a seizure has generalized might also be important; this can frequently be determined by comparing electrographic activity observed with multiple distant sets of detection electrodes (by determining whether epileptiform activity is present in multiple parts of the patient's brain simultaneously), or by considering the characteristics of the activity itself (as above, with reference to propagated activity). Activity that has not yet generalized is treatable via electrical stimulation at or near the focus, as such stimulation will tend to disrupt the onset. However, previously generalized (or primarily generalized) seizure activity may be more effectively treated by alternative means targeting a functionally relevant portion of the patient's brain (or even the entire brain), such as responsive drug therapy or electrical stimulation of a brain structure such as the caudate nucleus. The caudate nucleus regulates cortical activity, and it has been found that stimulation of the head of the caudate nucleus can terminate seizures. See S Chkhenkeli et al., "Effects of Therapeutic Stimulation of Nucleus Caudatus on Epileptic Electrical Activity of Brain in Patients with Intractable Epilepsy," Stereotact. Funct. Neurosurg., 69: 221-224 (1997). Other examples will be set forth below.

Active measurement of electrophysiological conditions is an emerging and promising factor in identifying and treating seizures and their onsets. See U.S. patent application Ser. No. 09/706,322, filed Nov. 3, 2000, which is hereby incorporated by reference as though set forth in full herein; it includes a detailed description of possible electrophysiological measurement methods advantageously employed in the context of the some embodiments. Electrophysiological conditions can be used alone (as in the reference cited above) or in combination with events detected by other means to guide treatment. For example, when excitation or inhibition is found to be abnormal, a certain onset pattern may be particularly likely to result in a full-blown clinical seizure, warranting more aggressive treatment than would be ordinarily attempted in the absence of the electrophysiological condition. In particular, trends and historical electrophysiological behavior are expected to provide particularly valuable information.

Finally, there is a practically limitless number of possible other measurements and observations that can be made using various sensors in connection with a system according to various embodiments, such as for temperature, blood pressure, sleep or arousal state, cerebral blood flow rate, blood oxygenation, drug concentration, neurotransmitter concentration, orientation (for detecting rest or sleep), or acceleration or angular velocity (particularly advantageous for use in connection with movement disorders). Factors observable by any or all of these sensors can be used advantageously to drive therapy decisions by a system according to the various embodiments. Sleep or arousal state, for example (as determined electrographically, via other sensor measurements, or inferred from data such as time of day and orientation) may be advantageously used to control the aggressiveness of certain therapies, as a patient may be more or less likely to suffer a seizure (or other neurological event) when asleep.

System state observations, such as whether programmed or responsive therapy has been applied recently, whether multiple detections have occurred within a short period of time, the elapsed time since a detection or therapy, or the time of day (to name a few simple examples) might also be used to alter therapy delivery according to the some embodiments. Elapsed time, in particular, can be used to guide the aggressiveness of therapy, for example to provide a more sustained response when there has been a relatively long time since the last event.

As will be described in greater detail below, all of these possibilities are considered to be within the scope of and consistent with various embodiments described herein.

A neurostimulator 110 according to an embodiment, as it is implanted intracranially, is illustrated in detail in FIG. 1. The neurostimulator 110 is affixed in the patient's cranium 112 by way of a ferrule 118. The ferrule 118 is a structural member adapted to fit into a cranial opening, attach to the cranium 112, and retain the neurostimulator 110.

To implant the neurostimulator 110, a craniotomy is performed in the parietal bone anterior to the lambdoidal suture 114 to define an opening 120 slightly larger than the neurostimulator 110. The ferrule 118 is inserted into the opening 120 and affixed to the cranium 112, ensuring a tight and secure fit. The neurostimulator 110 is then inserted into and affixed to the ferrule 118.

As shown in FIG. 1, the neurostimulator 110 includes a lead connector 122 adapted to receive one or more electrical leads, such as a first lead 124. The lead connector 122 acts to physically secure the lead 124 to the neurostimulator 110, and facilitates electrical connection to a conductor in the lead 124 coupling an electrode to circuitry within the neurostimulator 110. The lead connector 122 accomplishes this in a substantially fluid-tight environment with biocompatible materials.

The lead 124, as illustrated, and other leads for use in a system or method in some embodiments, is a flexible elongated member having one or more conductors. As shown, the lead 124 is coupled to the neurostimulator 110 via the lead connector 122, and is generally situated on the outer surface of the cranium 112 (and under the patient's scalp), extending between the neurostimulator 110 and a burr hole 126 or other cranial opening, where the lead 124 enters the cranium 112 and is coupled to at least one depth or cortical electrode implanted in a desired location in or on the patient's brain. If the length of the lead 124 is substantially greater than the distance between the neurostimulator 110 and the burr hole 126, any excess may be urged into a coil configuration under the scalp. As described in U.S. Pat. No. 6,006,124 to Fischell, et al., which is hereby incorporated by reference as though set forth in full herein, the burr hole 126 is sealed after implantation to prevent further movement of the lead 124; in an embodiment, a burr hole cover apparatus is affixed to the cranium 112 at least partially within the burr hole 126 to provide this functionality.

The neurostimulator 110 includes a durable outer housing 128 fabricated from a biocompatible material. Titanium, which is light, extremely strong, and biocompatible, is used in analogous devices, such as cardiac pacemakers, and would serve advantageously in this context. As the neurostimulator 110 is self-contained, the housing 128 encloses a battery and any electronic circuitry necessary or desirable to provide the functionality described herein, as well as any other features. As will be described further below, a telemetry coil or other antenna may be provided outside of the housing 128 (and potentially integrated with the lead connector 122) to facilitate communication between the neurostimulator 110 and external devices.

The neurostimulator configuration described herein and illustrated in FIG. 1 provides several advantages over alternative designs. First, the self-contained nature of the neurostimulator substantially decreases the need for access to the neurostimulator 110, allowing the patient to participate in normal life activities. Its small size and intracranial placement causes a minimum of cosmetic disfigurement. The neurostimulator 110 will fit in an opening in the patient's cranium, under the patient's scalp with little noticeable protrusion or bulge. The ferrule 118 used for implantation allows the craniotomy to be performed and fit verified without the possibility of breaking the neurostimulator 110, and also provides protection against the neurostimulator 110 being pushed into the brain under external pressure or impact. A further advantage is that the ferrule 118 receives any cranial bone growth, so at explant, the neurostimulator 110 can be replaced without removing any bone screws—only the fasteners retaining the neurostimulator 110 in the ferrule 118 need be manipulated.

Other implantation configurations and methods of attachment are, of course, possible. In particular, it should be recognized that the neurostimulator 110 can be intracranially attached in other ways than using a ferrule, or might be sufficiently thin to be located under the patient's scalp without the need for a craniotomy. It is also possible to implant a neurostimulator 110 according to an embodiment in locations other than the patient's head 116; for example, a pectorally-implanted unit might have relatively longer leads that extend to the desired locations in and around the patient's brain.

Figure 2:
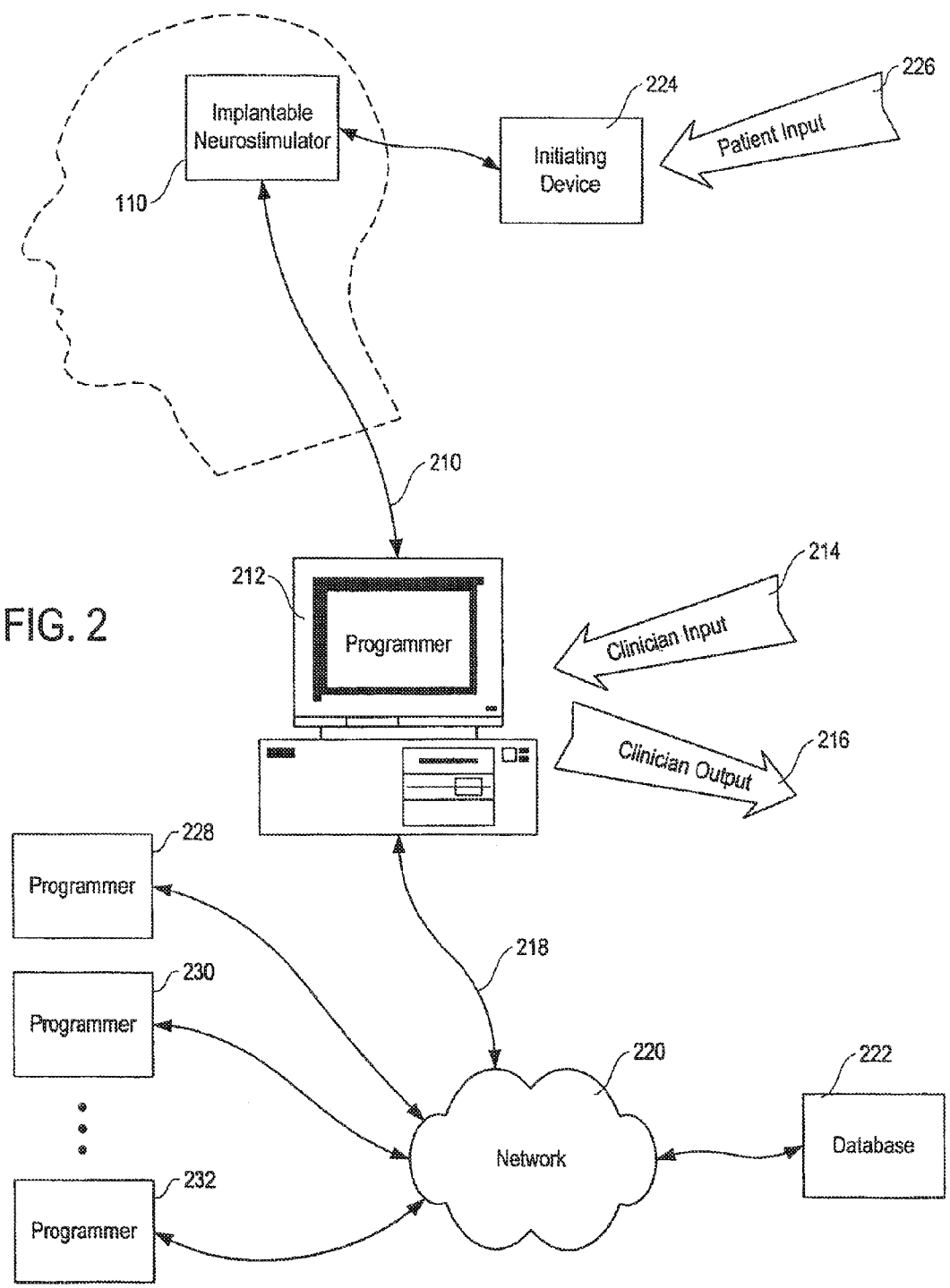
FIG. 2 is a block diagram illustrating a context in which an implantable neurostimulator according to an embodiment is implanted and operated, including various items of external equipment.

As stated above, and as illustrated in FIG. 2, a neurostimulator according to an embodiment operates in conjunction with external equipment. The implantable neurostimulator 110 is mostly autonomous (particularly when performing its usual sensing, detection, and stimulation capabilities), but preferably includes a selectable part-time wireless link 210 to external equipment such as a programmer 212. In an embodiment, the wireless link 210 is established by moving a wand (or other apparatus) having communication capabilities and coupled to the programmer 212 into communication range of the implantable neurostimulator 110. The programmer 212 can then be used to manually control the operation of the device, as well as to transmit information to or receive information from the implantable neurostimulator 110. Several specific capabilities and operations performed by the programmer 212 in conjunction with the device will be described in further detail below.

The programmer 212 is capable of performing a number of advantageous operations in connection with some embodiments. In particular, the programmer 212 is able to specify and set variable parameters in the implantable neurostimulator 110 to adapt the function of the device to meet the patient's needs, upload or receive data (including but not limited to stored EEG waveforms, parameters, or logs of actions taken) from the implantable neurostimulator 110 to the programmer 212, download or transmit program code and other information from the programmer 212 to the implantable neurostimulator 110, or command the implantable neurostimulator 110 to perform specific actions or change modes as desired by a physician operating the programmer 212. To facilitate these functions, the programmer 212 is adapted to receive clinician input 214 and provide clinician output 216; data is transmitted between the programmer 212 and the implantable neurostimulator 110 over the wireless link 210.

The programmer 212 may be used at a location remote from the implantable neurostimulator 110 if the wireless link 210 is enabled to transmit data over long distances. For example, the wireless link 210 may be established by a short-distance first link between the implantable neurostimulator 110 and a transceiver, with the transceiver enabled to relay communications over long distances to a remote programmer 212, either wirelessly (for example, over a wireless computer network) or via a wired communications link (such as a telephonic circuit or a computer network).

The programmer 212 may also be coupled via a communication link 218 to a network 220 such as the Internet. This allows any information uploaded from the implantable neurostimulator 110, as well as any program code or other information to be downloaded to the implantable neurostimulator 110, to be stored in a database 222 at one or more data repository locations (which may include various servers and network-connected programmers like the programmer 212). This would allow a patient (and the patient's physician) to have access to important data, including past treatment information and software updates, essentially anywhere in the world that there is a programmer (like the programmer 212) and a network connection. Alternatively, the programmer 212 may be connected to the database 222 over a trans-telephonic link.

In some embodiments, the wireless link 210 from the implantable neurostimulator 110 may enable a transfer of data from the neurostimulator 110 to the database 222 without any involvement by the programmer 212. In these embodiments, the wireless link 210 may be established by a short-distance first link between the implantable neurostimulator 110 and a transceiver, with the transceiver enabled to relay communications over long distances to the database 222, either wirelessly (for example, over a wireless computer network) or via a wired communications link (such as trans-telephonically over a telephonic circuit, or over a computer network).

In some embodiments, the implantable neurostimulator 110 is also adapted to receive communications from an initiating device 224, typically controlled by the patient or a caregiver. Accordingly, patient input 226 from the initiating device 224 is transmitted over a wireless link to the implantable neurostimulator 110; such patient input 226 may be used to cause the implantable neurostimulator 110 to switch modes (on to off and vice versa, for example) or perform an action (e.g., store a record of EEG data). Preferably, the initiating device 224 is able to communicate with the implantable neurostimulator 110 through the communication subsystem 130 (FIG. 1), and possibly in the same manner the programmer 212 does. The link may be unidirectional (as with the magnet and GMR sensor described above), allowing commands to be passed in a, single direction from the initiating device 224 to the implantable neurostimulator 110, but in some embodiments is bi-directional, allowing status and data to be passed back to the initiating device 224. Accordingly, the initiating device 224 may be a programmable PDA or other hand-held computing device, such as a Palm Pilot®. or PocketPC®. However, a simple form of initiating device 224 may take the form of a permanent magnet, if the communication subsystem 130 is adapted to identify magnetic fields and interruptions therein as communication signals.

In some embodiments, the programmer 212 is primarily a commercially available PC, laptop computer, or workstation having a CPU, keyboard, mouse and display, and running a standard operating system such as Microsoft Windows®, Linux®, Unix®, or Apple Mac OS®. It is also envisioned that a dedicated programmer apparatus with a custom software package (which may not use a standard operating system) could be developed.

When running the computer workstation software operating program, the programmer 212 can process, store, play back and display on the display the patient's EEG signals, as previously stored by the implantable neurostimulator 110 of the implantable neurostimulator device.

The computer workstation software operating program also has the capability to simulate the detection and prediction of sensor signal activity representative of movement disorders, such as the tremor described herein. Included in that capability, the software operating program may have the capability to allow a clinician to create or modify a patient-specific collection of information comprising, in one embodiment, algorithms and algorithm parameters for the detection of relevant sensor signal activity. The patient-specific collection of detection algorithms and parameters used for neurological activity detection in some embodiments will be referred to herein as a detection template or patient-specific template. The patient-specific template, in conjunction with other information and parameters generally transferred from the programmer to the implanted device (such as stimulation parameters, time schedules, and other patient-specific information), make up a set of operational parameters for the neurostimulator.

Following the development of a patient specific template on the workstation 212, the patient-specific template would be downloaded through the communications link 210 from the programmer 212 to the implantable neurostimulator 110.

The patient-specific template is used by the detection subsystem 122 and the CPU 128 of the implantable neurostimulator 110 to detect activity representative of a symptom of a movement disorder in the patient's EEG signals (or other sensor signals), which can be programmed by a clinician to result in responsive stimulation of the patient's brain, as well as the storage of EEG records before and after the detection, facilitating later clinician review.

In some embodiments, the database 222 is adapted to communicate over the network 220 with multiple programmers, including the programmer 212 and additional programmers 228, 230, and 232. It is contemplated that programmers will be located at various medical facilities and physicians' offices at widely distributed locations. Accordingly, if more than one programmer has been used to upload EEG records from a patient's implantable neurostimulator 110, the EEG records will be aggregated via the database 222 and available thereafter to any of the programmers connected to the network 220, including the programmer 212.

Figure 3:
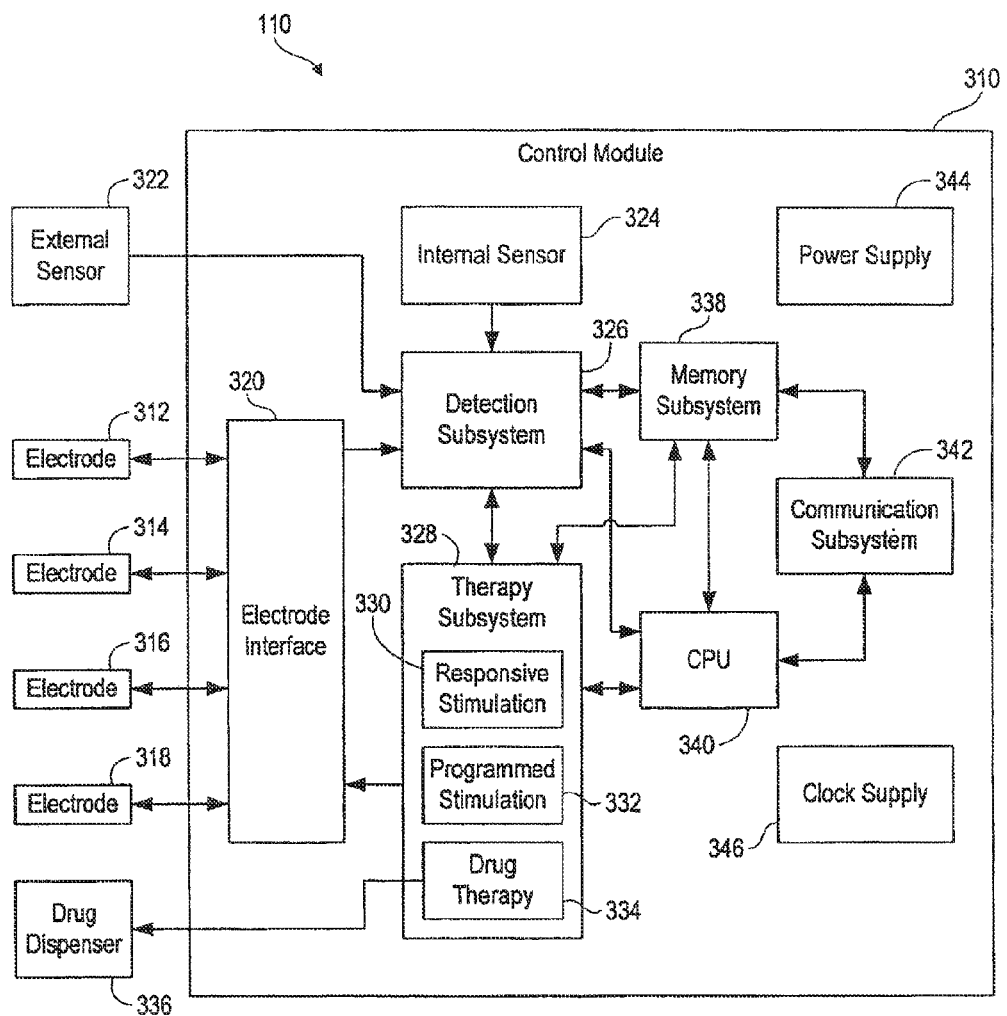
FIG. 3 is a block diagram illustrating the major functional subsystems of an implantable neurostimulator according to an embodiment.

An overall block diagram of the neurostimulator 110 used for measurement, detection, and treatment in some embodiments is illustrated in FIG. 3. Inside the housing 128 (FIG. 1) of the neurostimulator 110 are several subsystems making up a control module 310. The control module 310 is capable of being coupled to a plurality of electrodes 312, 314, 316, and 318 (each of which may be connected to the control module 310 via a lead for sensing, stimulation, or both. In the illustrated embodiment, the coupling is accomplished through the lead connector 122 (FIG. 1). Although four electrodes are shown in FIG. 3, it should be recognized that any number is possible, and in the embodiment described in detail below, eight electrodes are used. In fact, it is possible to employ an embodiment that uses a single lead with at least two electrodes, or two leads each with a single electrode (or with a second electrode provided by a conductive exterior portion of the housing 128 in one embodiment), although bipolar sensing between two closely spaced electrodes on a lead is preferred to minimize common mode signals including noise.

The electrodes 312-318 are connected to an electrode interface 320. In some embodiments, the electrode interface is capable of selecting each electrode as required for sensing and stimulation. The electrode interface 320 also may provide any other features, capabilities, or aspects, including but not limited to amplification, isolation, and charge-balancing functions, that are required for a proper interface with neurological tissue and not provided by any other subsystem of the neurostimulator 110. The electrode interface 320, an external sensor 322, and an internal sensor 324 are all coupled to a detection subsystem 326; the electrode interface 320 is also connected to a therapy subsystem 328.

The detection subsystem 326 includes an EEG analyzer function. The EEG analyzer function, which will be described in greater detail below, is adapted to receive EEG and other signals from the electrodes 312-318, through the electrode interface 320, and to process those signals to identify neurological activity indicative of a seizure, a seizure onset, or any other neurological activity of interest; various inventive methods for performing such detection are described in detail below.

The detection subsystem may optionally also contain further sensing and detection capabilities, including but not limited to parameters derived from other physiological conditions (such as electrophysiological parameters, temperature, blood pressure, etc.), which may be sensed by the external sensor 322 or the internal sensor 324. These conditions will be discussed in additional detail below. In particular, it may be advantageous to provide an accelerometer, an angular velocity sensor, or an EMG sensing electrode as the external sensor at a location remote from the implantable neurostimulator 110 (e.g., in the case of a movement disorder, in one of the patient's limbs that is subject to tremor). The external sensor 322 can be connected to the neurostimulator 110 (and the detection subsystem 326) by a lead or by wireless communication, such as a wireless intrabody signaling technique. To detect head tremor, a clinical seizure, or orientation (e.g., for sleep detection), an accelerometer might be used as the internal sensor 324. Other sensors, such as for temperature, blood pressure, blood oxygenation, drug concentration, or neurotransmitter concentration might be implemented as part of the external sensor 322 or the internal sensor 324. Other sensor configurations are of course possible and are considered to be usable in various embodiments.

The therapy subsystem 328 is primarily capable of applying electrical stimulation to neurological tissue through the electrodes 312-318. This can be accomplished in any of a number of different manners. For example, it may be advantageous in some circumstances to provide stimulation in the form of a substantially continuous stream of pulses, or on a scheduled basis. This form of stimulation, referred to herein as programmed stimulation, is provided by a programmed stimulation function 332 of the therapy subsystem 328. Preferably, therapeutic stimulation is also provided in, response to abnormal events detected by the data analysis functions of the detection subsystem 326. This form of stimulation, namely responsive stimulation, is provided by a responsive stimulation function 330 of the therapy subsystem 328.

As illustrated in FIG. 3, the therapy subsystem 328 and the data analysis functions of the detection subsystem 326 are in communication; this facilitates the ability of therapy subsystem 328 to provide responsive stimulation as well as an ability of the detection subsystem 326 to blank the amplifiers while stimulation is being performed to minimize stimulation artifacts. It is contemplated that the parameters of the stimulation signal (e.g., frequency, duration, waveform) provided by the therapy subsystem 328 would be specified by other subsystems in the control module 310, as will be described in further detail below.

In some embodiments, the therapy subsystem 328 is also capable of a drug therapy function 334, in which a drug is dispensed from a drug dispenser 336 (which may be integral with the control module 310 or an external unit). As with electrical stimulation, this capability can be provided either on a programmed basis (or continuously) or responsively, after an event of some kind is detected by the detection subsystem 326.

Also in the control module 310 is a memory subsystem 338 and a central processing unit (CPU) 340, which can take the form of a microcontroller. The memory subsystem 338 is coupled to the detection subsystem 326 (e.g., for receiving and storing data representative of sensed EEG signals and other sensor data), the therapy subsystem 328 (e.g., for providing stimulation waveform parameters to the stimulation subsystem), and the CPU 340, which can control the operation of the memory subsystem 338. In addition to the memory subsystem 338, the CPU 340 is also connected to the detection subsystem 326 and the therapy subsystem 328 for direct control of those subsystems.

Also provided in the control module 310, and coupled to the memory subsystem 338 and the CPU 340, is a communication subsystem 342. The communication subsystem 434 enables communication between the implantable neurostimulator 110 (FIG. 1) and the outside world, particularly the external programmer 212 (FIG. 2). As set forth above, in some embodiments, the communication subsystem 342 includes a telemetry coil (which may be situated outside of the housing 128) enabling transmission and reception of signals, to or from an external apparatus, via inductive coupling.

Alternative embodiments of the communication subsystem 342 could use an antenna for an RF link or an audio transducer for an audio link (which, as described below, can also serve as an audio warning transducer).

Rounding out the subsystems in the control module 310 are a power supply 344 and a clock supply 346. The power supply 344 supplies the voltages and currents necessary for each of the other subsystems. The clock supply 346 supplies substantially all of the other subsystems with any clock and timing signals necessary for their operation.

It should be observed that while the memory subsystem 338 is illustrated in FIG. 3 as a separate functional subsystem, the other subsystems may also require various amounts of memory to perform the functions described above and others. Furthermore, while the control module 310 is preferably a single physical unit contained within a single physical enclosure, namely the housing 128 (FIG. 1), it may comprise a plurality of spatially separate units each performing a subset of the capabilities described above. Also, it should be noted that the various functions and capabilities of the subsystems described above may be performed by electronic hardware, computer software (or firmware), or a combination thereof. The division of work between the CPU 340 and the other functional subsystems may also vary—the functional distinctions illustrated in FIG. 3 may not reflect the integration of functions in a real-world system or method in some embodiments.

The implantable neurostimulator 110 (FIG. 1) generally interacts with the programmer 212 (FIG. 2) as described below. Data stored in the memory subsystem 338 can be retrieved by the patient's physician through the wireless communication link 210, which operates through the communication subsystem 342 of the implantable neurostimulator 110. In connection with some embodiments, a software operating program run by the programmer 212 allows the physician to read out a history of events detected including EEG information before, during, and after each event, as well as specific information relating to the detection of each event (such as, in one embodiment, the time-evolving energy spectrum of the patient's EEG). The programmer 212 also allows the physician to specify or alter any programmable parameters of the implantable neurostimulator 110. The software operating program also includes tools for the analysis and processing of recorded EEG records to assist the physician in developing optimized tremor detection parameters for each specific patient, and to identify which therapies in conjunction with some embodiments are most advantageously associated with what event characteristics.

Figure 4:
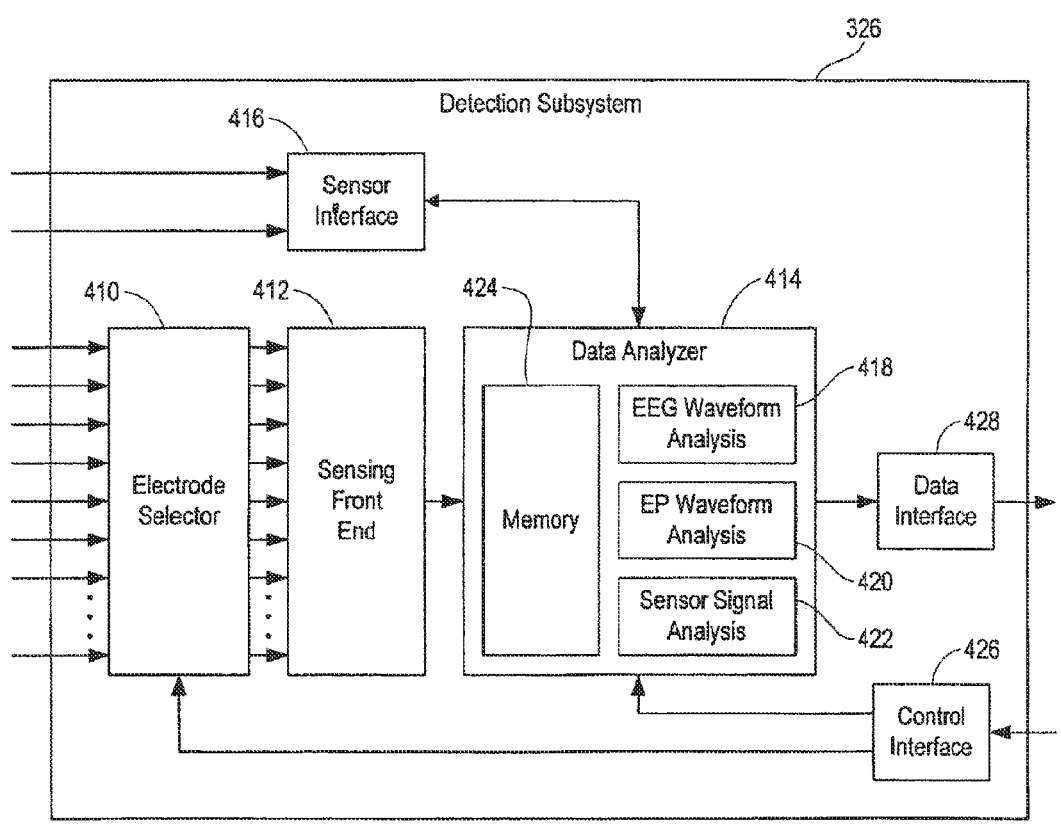
FIG. 4 is a block diagram illustrating the functional components of the detection subsystem of the implantable neurostimulator shown in FIG. 3.

FIG. 4 illustrates details of the detection subsystem 326 (FIG. 3). Inputs from the electrodes 312-318 are on the left, and connections to other subsystems are on the right.

Signals received from the electrodes 312-318 (as routed through the electrode interface 320) are received in an electrode selector 410. The electrode selector 410 allows the device to select which electrodes (of the electrodes 312-318) should be routed to which individual sensing channels of the detection subsystem 326, based on commands received through a control interface 426 from the memory subsystem 338 or the CPU 340 (FIG. 3). Preferably, each sensing channel of the detection subsystem 326 receives a bipolar signal representative of the difference in electrical potential between two selectable electrodes.

Accordingly, the electrode selector 410 provides signals corresponding to each pair of selected electrodes (of the electrodes 312-318) to a sensing front end 412, which performs amplification, analog to digital conversion, and multiplexing functions on the signals in the sensing channels. Preferably, any of the electrodes 312-318 can be unused (i.e., not connected to any sensing channel), coupled to a positive or negative input of a single sensing channel, coupled to the positive inputs of multiple sensing channels, or coupled to the negative inputs of multiple sensing channels.

A multiplexed input signal representative of all active sensing channels is then fed from the sensing front end 412 to a data analyzer 414. The data analyzer 414 is preferably a special-purpose digital signal processor (DSP) adapted for use in some embodiments, or in some alternative embodiments, may comprise a programmable general-purpose DSP.

In some embodiments, the data analyzer 414 is capable of performing three functions, namely, an EEG waveform analysis function 418, an electrophysiological waveform analysis function 420, and a sensor signal analysis function 422. It will be recognized that some or all of these functions can be performed with the same software or hardware in the data analyzer 414, by simply operating with different parameters on different types of input data. It is also possible, of course, to combine the three functions in many ways to detect neurological events or conditions, or to identify event characteristics in connection with some embodiments.

In some embodiments, the data analyzer has its own scratchpad memory area 424 used for local storage of data and program variables when the signal processing is being performed.

In either case, the signal processor performs suitable measurement and detection methods described generally above and in greater detail below.

As described in U.S. patent application Ser. No. 09/896,092, filed on Jun. 28, 2001, which is hereby incorporated by reference as though set forth in full herein, a responsive neurostimulator in some embodiments is capable of using three different kinds of analysis tools in various combinations, namely a half wave analysis tool, a line length analysis tool, and an area analysis tool. There are preferably multiple instances of each analysis tool, each of which can be set up with different detection parameters and coupled to a different input sensing channel if desired.

The half wave analysis tool measures characteristics of an EEG signal related to the signal's dominant frequency content. In general terms, a half wave is an interval between a local waveform minimum and a local waveform maximum; each time a signal "changes directions" (from increasing to decreasing, or vice versa), subject to limitations that will be set forth in further detail below, a new half wave is identified.

The identification of half waves having specific amplitude and duration criteria allows some frequency-driven characteristics of the EEG signal to be considered and analyzed without the need for computationally intensive transformations of normally time-domain EEG signals into the frequency domain. Specifically, the half wave feature extraction capability identifies those half waves in the input signal having a duration that exceeds a minimum duration criterion and an amplitude that exceeds a minimum amplitude criterion. The number of half waves in a time window meeting those criteria is somewhat representative of the amount of energy in a waveform at a frequency below the frequency corresponding to the minimum duration criterion. And the number of half waves in a time window is constrained somewhat by the duration of each half wave (i.e., if the half waves in a time window have particularly long durations, relatively fewer of them will fit into the time window), that number is highest when a dominant waveform frequency most closely matches the frequency corresponding to the minimum duration criterion.

Accordingly, the number of qualified half waves (i.e., half waves meeting both the duration criterion and the amplitude criterion) within a limited time period is a quantity of interest, as it may be representative of neurological events manifested in the specified frequency range corresponding to the half wave criteria. The half wave analysis tool, particularly when used on filtered EEG data, can be used to identify the presence of signals in a particular desired frequency range.

The line length analysis tool is a simplification of waveform fractal dimension, allowing a consideration of how much variation an EEG signal undergoes. Accordingly, the line length analysis tool in some embodiments enables the calculation of a "line length" for an EEG signal within a time window. Specifically, the line length of a digital signal represents an accumulation of the sample-to-sample amplitude, variation in the EEG signal within a time window. Stated another way, the line length is representative of the variability of the input signal. A constant input signal will have a line length approaching zero (representative of substantially no variation in the signal amplitude), while an input signal that oscillates between extrema from sample to sample will approach the maximum line length. It should be noted that while "line length" has a mathematical-world analogue in measuring the vector distance travelled in a graph of the input signal, the concept of line length as treated herein disregards the horizontal (X) axis in such a situation. The horizontal axis herein is representative of time, which is not combinable in any meaningful way in some embodiments with information relating to the vertical (Y) axis, generally representative of amplitude, and which in any event would contribute nothing of interest.

The area analysis tool is a simplification of waveform energy. Accordingly, the area analysis tool in some embodiments enables the calculation of the area under the EEG waveform curve within a time window. Specifically, the area function is calculated as an aggregation of the EEG's signal total deviation from zero over the time window, whether positive or negative. The mathematical-world analogue for the area function is the mathematical integral of the absolute value of the EEG function (as both positive and negative signals contribute to positive energy). Once again, the horizontal axis (time) makes no contribution to the area under the curve as treated herein. Accordingly, an input signal that remains around zero will have a small area, while an input signal that remains around the most-positive or most-negative values (or oscillates between those values) will have a high area.

Any of the three detection tools summarized above (and described in detail in U.S. patent application Ser. No. 09/896,092, filed on Jun. 28, 2001) can be used in connection with any of the three functions of the data analyzer 414, and can be easily tuned to operate on essentially any kind of source data.

In some embodiments, the data analyzer 414 is adapted to derive parameters from an input signal not only for detection purposes, but also to achieve the desired stimulation timing in some embodiments. It is useful for a data analyzer 414 in some embodiments to have multiple mappable channels, allowing at least a single channel to be configured specifically to derive signal timing for adaptive stimulation signal synchronization, and other channels to be used for event detection. See U.S. patent application Ser. No. 09/896,092, referenced above, for details on a multi-channel detection subsystem programmable as described herein.

The half wave analysis tool is particularly useful for providing adaptive stimulation parameters in some embodiments, as qualified half waves derived as set forth above are discrete and identifiable features of an electrographic waveform that, have well-defined amplitudes, durations, and start and end times that are advantageously mappable to stimulation signal characteristics.

There are multiple instances and channels of half wave analysis tools, as described above, and the multiple instances can analyze separate input channels with different signal processing and detection parameters. It should be noted that this capability is particularly advantageous in some embodiments, as certain signal processing and half wave detection parameters may be used for neurological event detection and others used for synchronization and adaptive stimulation as described herein. In particular, certain qualified half waves, namely those signal half waves meeting minimum amplitude and minimum duration criteria useful for event detection, may not be best suited for stimulation timing. Therefore, in some embodiments, one instance of the half wave analysis tool is dedicated to deriving qualified half waves specifically for use as synchronization points for adaptive stimulation, as will be described in further detail below. This half wave analysis tool can receive either the same signal that is used for detection or a different signal, depending on how the neurostimulator device 110 is programmed and configured.

Any results from the detection methods described above, as well as any digitized signals intended for storage and subsequent transmission to external equipment, are passed to various other subsystems of the control module 310, including the memory subsystem 338 and the CPU 340 (FIG. 3) through a data interface 428. Similarly, the control interface 426 allows the data analyzer 414 and the electrode selector 410 to be in communication with the CPU 340.

Again, the functional distinctions illustrated in FIG. 4, which are presented as separate functions for clarity and understandability herein, might not be meaningful distinctions in some embodiments.

Figure 5:
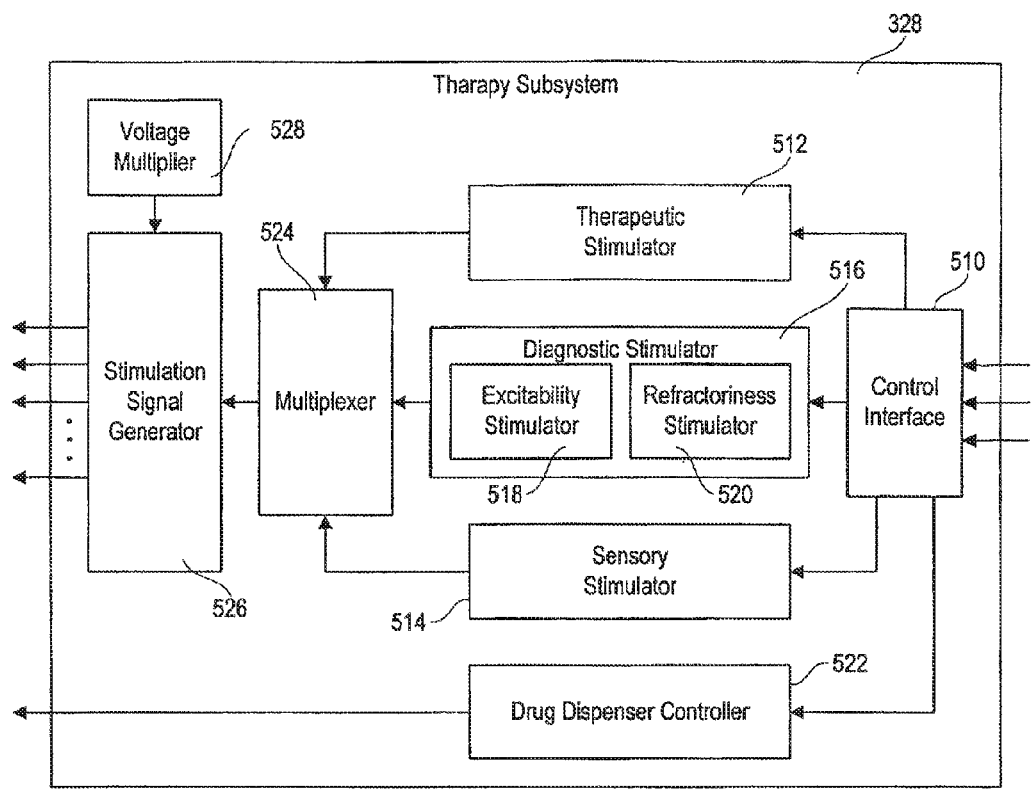
FIG. 5 is a block diagram illustrating the functional components of the therapy subsystem of the implantable neurostimulator shown in FIG. 3.

The various functions and capabilities of the therapy subsystem 328 (FIG. 3) are illustrated in greater detail in FIG. 5. Consistent with FIG. 4, inputs to the therapy subsystem 328 are shown on the right, and outputs are on the left.

Referring initially to the input side of FIG. 5, the stimulation subsystem 328 includes a control interface 510, which receives commands, data, and other information from the CPU 340, the memory subsystem 338, and the detection subsystem 326 (FIG. 3). The control interface 510 uses the received commands, data, and other information to control a therapeutic stimulator 512, a sensory stimulator 514, and a diagnostic stimulator 516. The therapeutic stimulator 512 is adapted to provide electrical stimulation signals appropriate for application to neurological tissue to terminate a present or predicted undesired neurological event, especially an epileptic seizure (or its precursor). As set forth above, the therapeutic stimulator 512 is typically activated in response to conditions detected by the sensing subsystem 522, but may also provide some substantially continuous or programmed or scheduled stimulation. The sensory stimulator 514 is also typically activated in response to a detection by the sensing subsystem; it may electrically stimulate enervated tissue (such as the scalp) to provide a tactile sensation to the patient, or may alternatively include an audio or visual transducer to provide audiovisual cues (such as warnings) to the patient.

The diagnostic stimulator 516, which is used to perform active electrophysiological diagnostic measurements in connection with some embodiments, includes two sub-functions, an excitability stimulator 518 and a refractoriness stimulator 520, though both functions may be performed by the same circuit under differing controls from the control interface 510. The excitability stimulator 518 and the refractoriness stimulator 520 both act under the control of the detection subsystem 326 to provide the stimulation signals used for the effective measurement of electrophysiological parameters in some embodiments. In one embodiment, the excitability stimulator 518 provides pulses at varying current levels to test the excitability of neural tissue, while the refractoriness stimulator 520 provides pairs of pulses with varying inter-pulse intervals to test the inhibitory characteristics of neural tissue. For details on how active electrophysiological diagnostics are performed as used herein, see U.S. patent application Ser. No. 09/706,322, filed on Nov. 3, 2000, which is hereby incorporated by reference as though set forth in full herein.

The therapy subsystem 328 also includes a drug dispenser controller 522, which under the control of the control interface 510 (and the memory subsystem 338, the CPU 340, and the detection subsystem 326), is adapted to selectively allow the release of a drug or other therapeutic agent from a drug dispenser 336 (which typically contains a reservoir) to one or more desired sites, within or near the patient's brain or elsewhere in the body. As with therapeutic stimulation described above, drug therapy can be performed on a responsive basis (i.e., in response to a detected neurological event or condition), on a substantially continuous basis, or as programmed or scheduled.

The therapeutic stimulator 512, the sensory stimulator 514, and the diagnostic stimulator 516 are all coupled to a multiplexer 524, which is controllable to select the appropriate types of stimulation and pass them along to a stimulation signal generator 526. The multiplexer 524 may allow only one type of stimulation to be performed at a time, but in some embodiments, the multiplexer 524 allows different types of stimulation to be selectively applied to the different electrodes 312-318, either sequentially or substantially simultaneously. The stimulation signal generator 526 receives commands and data from the therapeutic stimulator 512, the sensory stimulator 514, and the diagnostic stimulator 516, and generates electrical stimulation signals having the desired characteristics that are properly time-correlated and associated with the correct electrodes, and receives power from a controllable voltage multiplier 528 to facilitate the application of a proper voltage and current to the desired neurological tissue. The voltage multiplier 528 is capable of creating relatively high voltages from a battery power source, which typically has a very low voltage; circuits to accomplish this function are well known in the art of electronics design. The stimulation signal generator 526 has a plurality of outputs, which in the disclosed embodiment are coupled to the electrode interface 320 (FIG. 3). In various embodiments, the stimulation signal generator 526 can perform signal isolation, multiplexing, and queuing functions if the electrode interface 320 does not perform such functions.

It should be recognized that while various functional blocks are illustrated in FIG. 5, not all of them might be present in an operative embodiment. Furthermore, as with the overall block diagram of FIG. 3, the functional distinctions illustrated in FIG. 5, which are presented as separate functions for clarity and understandability herein, might not be meaningful distinctions in some embodiments. For example, in the presently preferred embodiment, the various stimulation types (provided in FIG. 5 by stimulators 512-516) are all accomplished with a single circuit selectively controlled with different parameters; there is a single controllable stimulator capable of selectively providing signals for therapeutic stimulation, diagnostic stimulation, and sensory stimulation.

Figure 6:
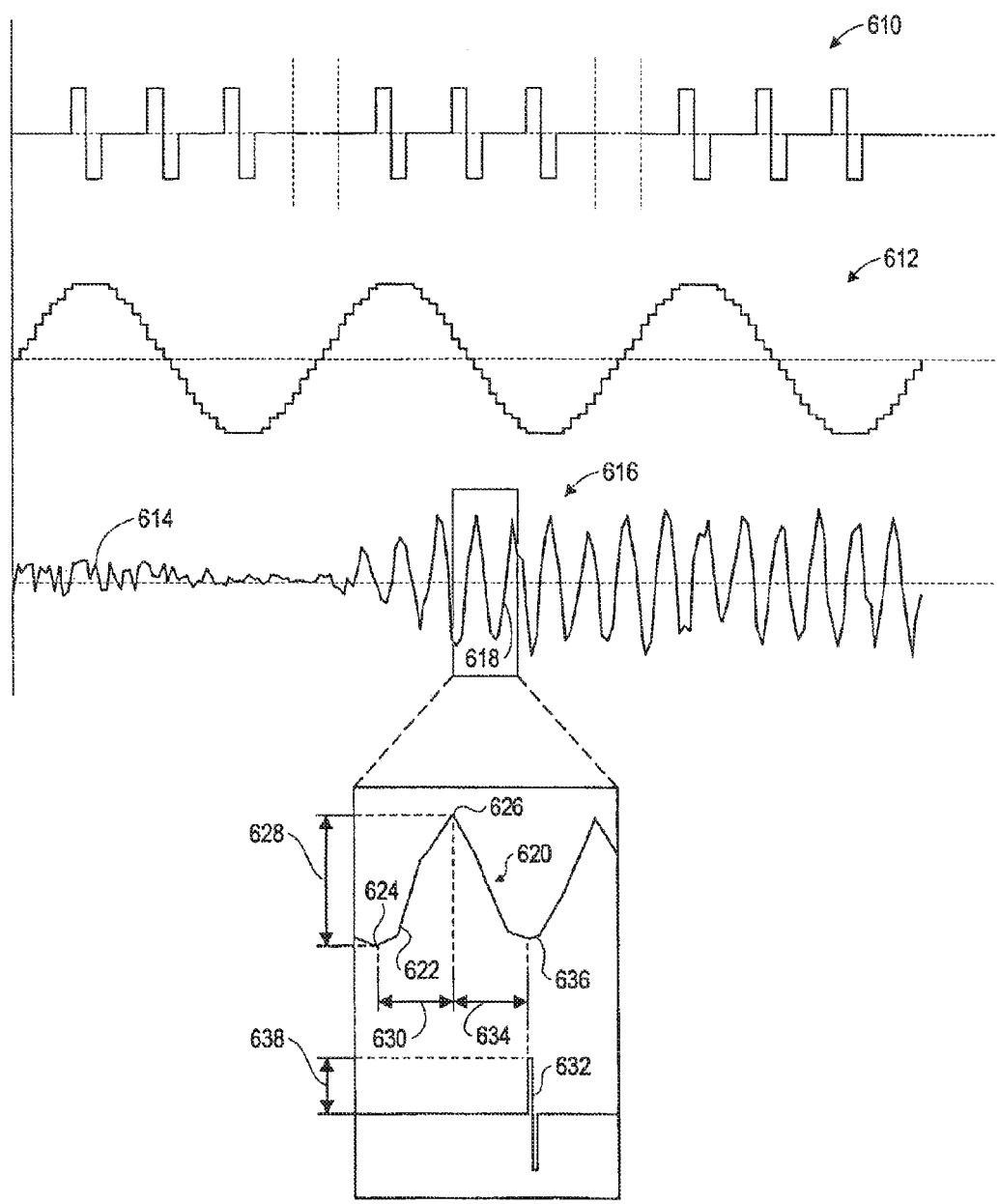
FIG. 6 illustrates several possible electrical stimulation modalities according to an embodiment.

Referring now to FIG. 6, a first modality of treatment, bursts of biphasic pulses, is illustrated by a first stimulation waveform 610. This type of stimulation has been found to be advantageously applied at or near a seizure focus upon detection of an onset to prevent a clinical seizure from occurring. It is also usable for programmed stimulation, at various amplitudes, to reduce susceptibility to undesired activity, and for acute stimulation at functionally relevant brain structures.

A second modality of treatment is illustrated by a second stimulation waveform 612, which generally represents a stepwise approximation of a sinusoidal signal. Such a signal can be applied to terminate certain kinds of epileptiform activity, as described above, or also potentially as a continuous, semi-continuous, or programmed sub-threshold stimulation to reduce susceptibility to seizures or other undesired activity. Although the second stimulation waveform 612 is illustrated as a digitally-generated approximation of a sinusoidal waveform, it should be recognized that waveforms more closely resembling sine waves (and true sine waves) might be applied instead; the stepwise approximation is advantageously used to leverage existing waveform playback and digital-to-analog conversion capabilities of a system according to some embodiments. Haversine and other smoothed signals might also be used to similar effect, with or without DC offset.

Finally, a third modality of stimulation therapy is illustrated in connection with an exemplary electrographic waveform 614, which is related to a stimulation pulse specially timed according to some embodiments. The electrographic waveform 614, which is of the general type that would be received and processed by the implantable neurostimulator 110 (via the electrodes 312-318, passed through the electrode interface 320 to the detection subsystem 326), has a seizure portion 616 that clearly visually represents rhythmic epileptiform activity. The specific characteristics of the waveform 614 are exemplary only and for purposes of illustration; they are not necessarily intended to reflect a possible real-world scenario. It should be noted in particular that although the seizure portion 616 of the electrographic waveform 614 is clearly apparent in FIG. 6, that would not necessarily be the case in an actual implementation of a system in some embodiments.

A small segment 618 of the seizure portion 616 is magnified and shown as a magnified segment 620. The magnified segment 620 will be used to illustrate the derivation of waveform characteristics of interest and the delivery of an adaptive stimulation signal according to some embodiments. As illustrated, an increasing half wave 622 represents a substantially monotonic (exclusive of a small hysteresis allowance) increasing portion of the magnified segment 620 between a local minimum 624 and a local maximum 626 of the waveform 614. The amplitude difference (on the Y axis) between the local minimum 624 and the local maximum 626 is the amplitude 628 of the half wave, and the time difference (on the X axis) between the local minimum 624 and the local maximum 626 is the duration 630 of the half wave. If the amplitude 628 and duration 630 exceed respective thresholds, then the observed half wave is considered a "qualified half wave," and is generally regarded as representative of the dominant frequency and amplitude of the electrographic waveform. If the observed half wave does not meet the thresholds, it is disregarded. For details on half wave measurement, see, e.g., U.S. patent application Ser. No. 09/896,092, referenced above. It should be noted that even if a qualified half wave meets minimum amplitude and duration thresholds, it is not necessarily truly representative of the underlying signal's frequency or wavelength; it is only a single measurement from what is likely a complex waveform.

As will be described in further detail below, once an event detection has been made, the amplitude 628 and duration 630 are used in various ways by a system according to some embodiments to synchronize or desynchronize a stimulation signal to the waveform 614.

As illustrated in FIG. 6, in an embodiment, a biphasic stimulation pulse 632 is applied after a time delay 634 equal in length to the duration 630, thereby approximately synchronizing the pulse 632 to an expected trough 636 in the waveform 614. It should be recognized, of course, that the duration of a qualified half wave is not necessarily accurately representative of the wavelength of the electrographic waveform 614 in the seizure portion 616 (because of variations in the waveform 614 and in the individual half waves making up the waveform 614), so in practice it is unlikely that the pulse 632 will be accurately synchronized to the trough 636. However, after a delay of only one additional half wave duration 630, it is expected that the pulse 632 and the trough 636 may be relatively close.

After a delay of multiple half wave durations, or after significant processing latency, by the neurostimulator 110 synchronization is less likely and decorrelation will generally be the primary outcome. Accordingly, if the time delay 634 is set to be a multiple (or some other mathematical transform) of the duration 630, or if there is a significant amount of latency between measurement of half wave amplitude 628 and duration 630 and when a stimulation pulse 632 is applied, the delay 634 will generally desynchronize stimulation from the waveform 614 as a result of accumulated error and changes in the characteristics of the waveform 614. As described above, in some embodiments, this may desirably serve as a variable factor in stimulation to decrease the likelihood of undesired learning of stimulation characteristics.

In an alternative embodiment, if desired, a pulse amplitude 638 can be correlated to the half wave amplitude 628 in a similar manner, or both amplitude 628 and duration 630 can be mapped onto a stimulation pulse.

It should be noted that while a single biphasic pulse 632 is illustrated in FIG. 6, that pulse is not necessarily to scale and is intended only to illustrate an exemplary timing relationship between the magnified segment 620 and the start of the pulse 632. The amplitude of the pulse 632 may not have the illustrated relationship to the waveform 614. And in an alternative embodiment, the pulse 632 may have a waveform other than a short biphasic pulse, or may be the first portion of a regular or irregular burst of pulses or other signals.

In connection with some embodiments, waveform parameters and other characteristics of an event can be used for at least two purposes: first, identifying the nature of the event and selecting the most effective therapy given the nature of the event; and second, correlating, decorrelating, or otherwise varying the therapy based on an observed parameter to provide enhanced therapy, as generally described in U.S. patent application Ser. No. 09/962,940, of which this application is a continuation-in-part.

Figure 7:
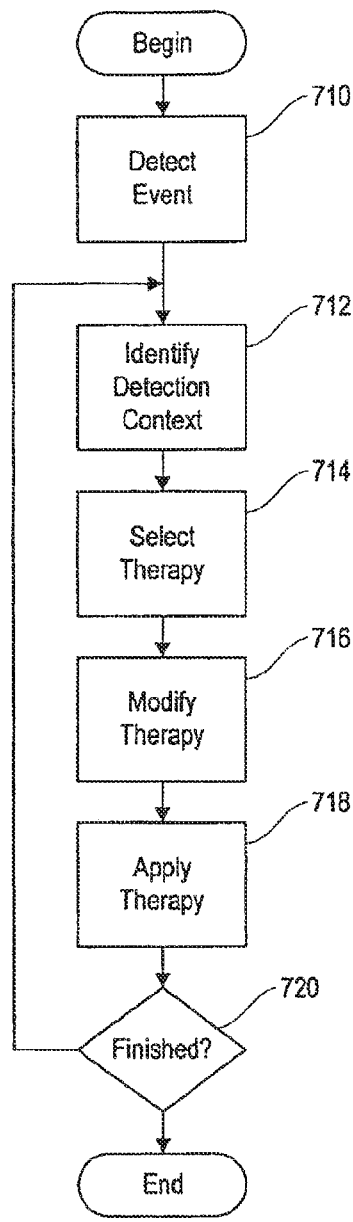
FIG. 7 is a flow chart illustrating a device-context-based approach to differential therapy according to an embodiment.

A method for applying differential therapy in some embodiments based in part on a "device context" is illustrated in FIG. 7. Device context, as the term is used herein, is some measurable or observable aspect, function, or parameter of the neurostimulator 110 that can be used to select a suitable therapy. One example of device context is which detection channel, of multiple detection channels, triggered an event detection by the neurostimulator 110.

Initially, a neurological event of interest is detected (step 710); this neurological event can be a seizure, a seizure onset, an episode of a movement disorder, an episode of pain, or any of numerous other possibilities. Once the event is detected, the context is identified (step 712). As described above, one possibility is which detection channel was triggered; other possibilities include time of day, the time since the last detection, the time since the last therapy delivery, physiological or system conditions, or numerous others.

Based on the context, which as observed by the neurostimulator 110 is generally a numeric quantity (e.g. elapsed time) or transformable into a numeric quantity (e.g. which detection channel), a therapy is selected (step 714) from a plurality of possible therapies. In some embodiments, the therapy most likely to treat the detected event most effectively (as determined by prior clinical testing, either patient-specific or generally) is associated with each possible numeric quantity or applicable ranges of quantities. In a relatively complex embodiment, the possible therapies include responsive electrical stimulation, initiation of a course of scheduled or programmed electrical stimulation, the release of a quantity of a drug or other therapeutic agent, or the delivery of a warning to the patient or another individual. There are other possibilities, and variations within those categories (such as the delivery of responsive electrical stimulation to various targets) that should be considered.

If desired, the selected therapy is then modified or otherwise transformed (step 716) based on the previously-identified context or any other value of interest. For example, if a burst of biphasic pulses is selected as the therapy, the frequency or amplitude, or duration of the burst can be modified in some embodiments. Therapy delivery is then scheduled, and therapy is applied by the neurostimulator 110 as specified (step 718). If the planned therapy delivery is incomplete (step 720), then additional context measurements can be performed (optionally), and therapy selection, modification, and application are repeated as necessary (steps 712-718).

As described above, device context can be used to differentiate between different types and locations of seizure onsets in some embodiments. If the neurostimulator 110 includes multiple active detection channels, each receiving a signal from a different portion of the patient's brain, then the identity of the triggering detection channel is directly related to the location of the detected event, and may also be related to the type of the detected event.

Accordingly, using device context according to the method set forth in FIG. 7 is consistent with one of the objectives of some embodiments, namely to treat different types and locations of events differently. Onset type and location may frequently be interrelated, as well; a patient may have one seizure (or other event) type that originates exclusively in a first location, while a second event type originates only elsewhere.

Other forms of device context (e.g., the elapsed time since the most recent event detection) also tend to be relevant, as different types of neurological events tend to be preceded by different kinds of activity.

In relation to the objectives of a system according to some embodiments, it should be observed that possible desired outcomes (depending on the triggering event) include avoiding or terminating an onset (if the detected event is a seizure or other event's onset), avoiding or terminating the result of the event (for example, if the event is a seizure onset or the seizure itself), halting the propagation of undesired activity (for example, if the detected event is a generalizing seizure), reducing the susceptibility of the patient to undesired activity (if the detected event is, for example, representative of a prediction or an increased likelihood of a seizure or other problem—such as interictal spiking), or delivering a warning (in any or all of the foregoing scenarios). Different therapy strategies may be applicable for each of these scenarios, and the neurostimulator 110 is preferably programmed to select the most effective course.

As recognized above, many different therapy types and subtypes are possible in various embodiments. Several permutations may be illustrative: responsive, continuous, or programmed electrical stimulation can be applied at or near the event's focus (with one or more of the following characteristics: pulses, sinusoidal waveforms, sub-threshold stimulation, DC stimulation, adaptively timing); responsive, continuous, or programmed electrical stimulation can be applied at or near the location where the activity was first detected (with one or more of the foregoing characteristics); responsive, continuous, or programmed electrical stimulation can be applied at a functionally relevant brain area (with one or more of the same possible characteristics), such as the caudate nucleus, the subthalamic nucleus, the anterior thalamus, the ventralateral thalamus, the globus pallidus internus, the globus pallidus externus, the substantia nigra, or the neostriatum (or any selected portion of any of these structures); responsive, continuous, or programmed electrical stimulation can be applied at a peripheral nerve, such as the vagus nerve, or any other desired location; drug therapy can be applied to any desired location (in the brain or bloodstream, for example); somatosensory stimulation or sensory stimulation (such as an audio signal) can be provided to the patient; or a message can be transmitted from the neurostimulator 110 to external equipment.

There are many other possibilities and permutations; they will not be described in detail herein, but would be apparent to a practitioner of ordinary skill. Two or more of these therapy types and subtypes can, of course, be combined into a single course of therapy, should it be clinically advantageous to do so.

Figure 8:
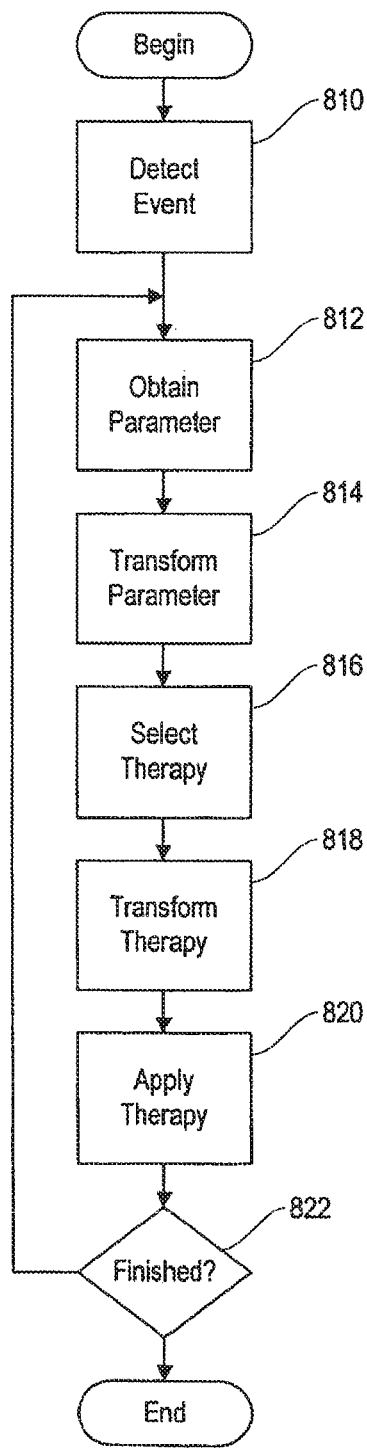
FIG. 8 is a flow chart illustrating a physiological-context-based approach to differential therapy according to an embodiment.

The method illustrated by the flow chart of FIG. 8 is analogous to the method of FIG. 7, but uses measurements and other parameters obtained by the neurostimulator 110, rather than device context, to drive therapy selection.

Initially, a neurological event of interest is detected (step 810); this neurological event can be a seizure, a seizure onset, an episode of a movement disorder, an episode of pain, or any of numerous other possibilities. Once the event is detected, a parameter relating to a characteristic of the detected event is obtained (step 812).

One advantageously utilized type of parameter is represented by data stored by the neurostimulator 110 in the course of its ordinary measurement and detection tasks, such as data related to EEG morphology. For example, to the extent the detection channels of the neurostimulator 110 store relatively unprocessed data (for example, half wave, line length, and area information) upon which detection decisions are made, this information may be advantageously used to derive a characteristic for any detected event. For example, after an event is detected, retrospective or prospective consideration of half wave densities, signal frequency content or variability, or other characteristics may provide useful information as to the nature of the detected event.

Other parameters include measurements performed by the neurostimulator 110, such as from the physical and physiological state sensors described above (temperature, blood pressure, orientation, etc.), and active electrophysiological measurements performed as described above and in connection with U.S. patent application Ser. No. 09/706,322, referenced above.

Details of some of these measurement techniques will be set forth in additional detail below, in connection with FIGS. 9-11.

It should be noted that not only measured parameters themselves, but trends and historical patterns in such parameters may also be indicative of a characteristic of the detected neurological event, and various embodiments are advantageously capable of obtaining, analyzing, and considering such trends and historical data as well.

After the parameter (or relevant trend or historical pattern) is obtained, the parameter is transformed (step 814) as desired, typically to map the parameter into a desired range or distribution of values. Based on the transformed parameter, then, a therapy is selected (step 816) from a plurality of possible therapies. As with the method of FIG. 7, above, the therapy most likely to treat the detected event most effectively is associated with each possible numeric parameter value or sub-range of values.

If desired, the selected therapy is then modified or otherwise transformed (step 818) based on the previously-measured parameter or any other value of interest. Therapy delivery is then scheduled, and therapy is applied by the neurostimulator 110 as specified (step 820). If the planned therapy delivery is incomplete (step 822), then additional measurements can be optionally performed, and the parameter transformation, therapy selection, modification, and application are repeated as necessary (steps 812-820).

It should be noted that it is, of course, possible to combine the approaches of FIG. 7 and FIG. 8 in a single treatment strategy. For example, a device context and a measured parameter (obtained in any way described above) can be combined into a single factor to select a course of therapy, or can be used individually to select and modify one or more therapy deliveries. Other possible combinations will be apparent.

Figure 9:
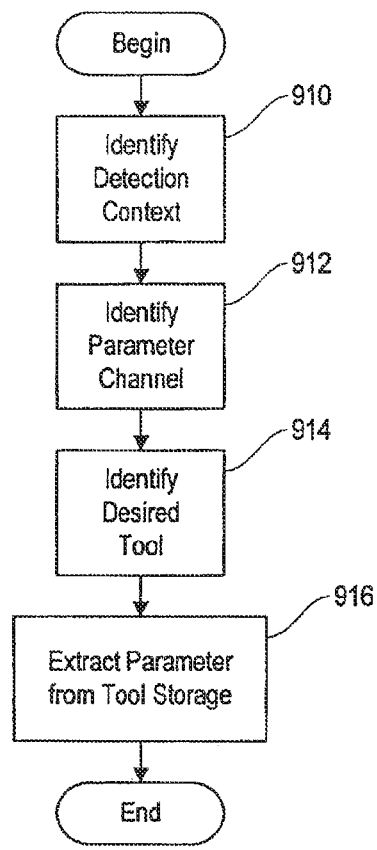
FIG. 9 is a flow chart illustrating the process performed by a system according to an embodiment in obtaining information about an event type from detection data stored by an implantable neurostimulator according to an embodiment.

A particularly effective use of the technology described herein (and the methods set forth in FIGS. 7-8, described above) is in relation to predicted events, namely to provide prophylactic therapy well in advance of any seizure onset or other clinically undesired event. In particular when the detection subsystem 326 (FIG. 3) is configured to detect a precursor to an event, or some other predictive circumstance that suggests or is representative of an increased probability of encountering the event, it may be advantageous to deliver a course of responsive therapy that is best tailored to avoid the event. In particular, it may be appropriate to consider the elapsed time since the last detection or therapy delivery to determine the aggressiveness of the response—if it has been a long time since the last event or therapy, or if physiological conditions dictate, it may be best to deliver a particularly strong and sustained response.

Where a parameter is to be measured from a queue or other storage associated with a detection channel (or elsewhere in the neurostimulator 110), one method for identifying that information is illustrated in FIG. 9.

Initially, a detection context is identified (step 910). As with the device context described above with reference to FIG. 7, the detection context is some observable aspect, function, or parameter of the neurostimulator 110 that relates to the detection. In some embodiments, the detection context comprises the detection channel that caused an event detection to take place (see step 810, FIG. 8). The context is then used to identify which channel it is desired to measure the event-related parameter from (step 912). In many circumstances, it may be desirable to observe and measure the parameter from the same channel that caused the detection (because that channel most like contains measurement data most closely related to the observed and detected event), but other channels, such as spatially adjacent channels or remote channels in a functionally relevant structure of the patient's brain, can also be used. Within the desired channel, the desired detection tool (half wave, line length, area, or any other applicable active technique) is selected (step 914); and the parameter is extracted from that detection tool's data storage (step 916). The parameter selected from a detection tool's storage can be representative of a signal's historical behavior, recent behavior in comparison to a trend, frequency content, or absolute value in comparison to a fixed or dynamic threshold. Various possible observations derived from detection tool data are described in detail in U.S. patent application Ser. No. 09/896,092, filed on Jun. 28, 2001, which is hereby incorporated by reference as though set forth in full herein; these possibilities will be apparent to a practitioner of ordinary skill.

It will be recognized that the parameter can then be used as illustrated in connection with FIG. 8, namely, to select and modify a course of therapy to effectively treat a detected seizure onset or other neurological event.

Figure 10:
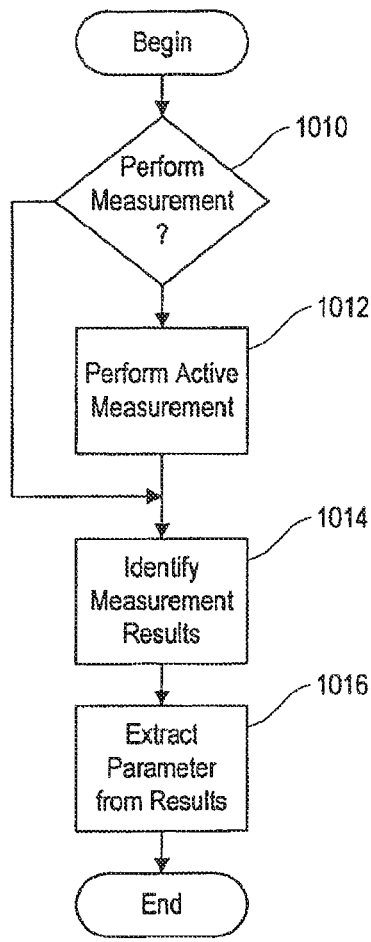
FIG. 10 is a flow chart illustrating the process performed by a system according to some embodiments in obtaining information about an event type from electrophysiology measurement data stored or otherwise acquired by an implantable neurostimulator according to an embodiment.

FIG. 10 illustrates how a parameter relating to an active electrophysiological measurement is obtained in some embodiments. Initially, if a new measurement is necessary (step 1010), e.g., if it has been longer than a specified elapsed time since the last electrophysiological measurement, then an active measurement of electrophysiological characteristics is performed (step 1012). As electrophysiological measurements involve computation by the neurostimulator 110 and the delivery of stimulation signals (see U.S. patent application Ser. No. 09/706,322, referenced above), it is desirable to perform a minimum number of measurements consistent with useful information; accordingly, measurements are not performed if they are not necessary.

The electrophysiological measurement results are then identified (step 1014) and any desired parameter is then extracted therefrom (step 1016). For example, electrophysiological excitability, refractoriness, or trends in either measurement may be used in some embodiments as the desired parameter, and then employed according to the method set forth in FIG. 8.

Figure 11:
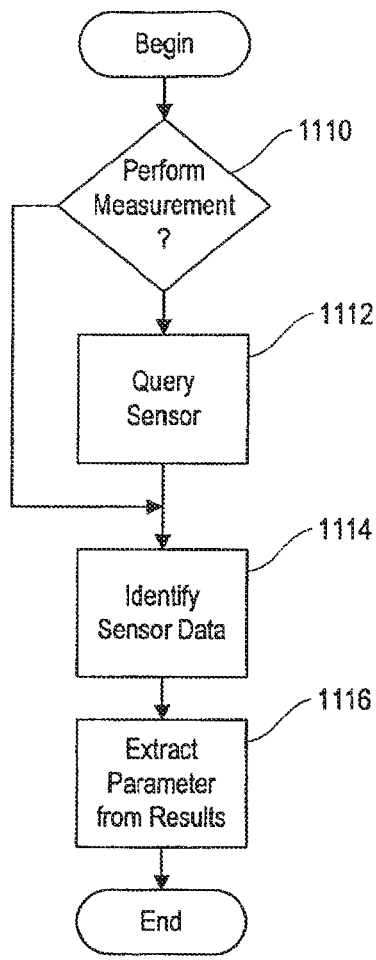
FIG. 11 is a flow chart illustrating the process performed by a system according to an embodiment in obtaining information about an event type from sensor measurement data stored or otherwise acquired by an implantable neurostimulator according to an embodiment.

Finally, FIG. 11 illustrates how a parameter related to a sensor signal is obtained in a system according to some embodiments.

As with the method of FIG. 10, if a new measurement is necessary (step 1110), e.g., if it has been longer than a specified elapsed time since the last sensor measurement, then the desired sensor is queried and a measurement is taken (step 1112). The processing of sensor measurements generally involves computation by the neurostimulator 110, and accordingly, it is desirable to perform a minimum number of sensor measurements consistent with maintaining useful and timely information; accordingly, as with electrophysiology, sensor measurements are not performed if they are not necessary.

The relevant sensor measurement results are then identified (step 1114), any desired parameter is then extracted therefrom (step 1116), and the measurement, trend, or historical pattern is then used in various embodiments as the desired parameter, and then employed according to the method set forth in FIG. 8.

Reference in the specification to "one embodiment", "an embodiment", "various embodiments" or "some embodiments" means that a particular feature, structure, or characteristic described in connection with these embodiments is included in at least one embodiment of the invention, and such references in various places in the specification are not necessarily all referring to the same embodiment.

It should be observed that while the foregoing detailed description of various embodiments is set forth in some detail, the invention is not limited to those details and an implantable neurostimulator or neurological disorder detection device made according to the invention can differ from the disclosed embodiments in numerous ways. In particular, it will be appreciated that embodiments may be employed in many different applications to effectively treat different types of seizure onsets and other neurological events. It will be appreciated that the functions disclosed herein as being performed by hardware and software, respectively, may be performed differently in an alternative embodiment. It should be further noted that functional distinctions are made above for purposes of explanation and clarity; structural distinctions in a system or method according to the invention may not be drawn along the same boundaries. Hence, the appropriate scope hereof is deemed to be in accordance with the claims as set forth below.

What is claimed is:

1. An implantable medical device system comprising:
    an implantable medical device configured to acquire EEG signals from a patient, to detect a neurological event of interest based on one or more EEG parameters derived from the EEG signals, and to store in a memory, a representation of the EEG signals, together with the one or more EEG parameters;
    an external component provided with a software operating program and associated hardware and configured to process, store, playback and display on a display of the external component the representation of the EEG signals and the one or more EEG parameters stored in the memory of the implantable medical device; and
    a communication link configured to establish communication between a communications subsystem of the implantable medical device and the external component to enable the external component to process, store, playback and display on the display of the external component the representation of the EEG signals acquired and stored in the implantable medical device;
    wherein the software operating program and associated hardware of the external component is configured to process the EEG signals received from the implantable medical device in order to simulate the detection of the neurological event.

2. The implantable medical device system of claim 1 wherein the communication link is a wireless link configured using a short distance first link between the implantable medical device and a transceiver, and the transceiver is configured to relay communications between the implantable medical device and the external component.

3. The implantable medical device system of claim 1 wherein the communication link is a wireless link configured using a long distance first link between the implantable medical device and a transceiver, and the transceiver is configured to relay information between the implantable medical device and the external component.

4. The implantable medical device system of claim 1 wherein the implantable medical device is further configured to acquire information corresponding to signal activity sensed by at least one sensor in operable communication with the implantable medical device, and the software operating program and associated hardware of the external component is further configured to process the signal activity received from the implantable medical device in order to simulate the detection and prediction of sensor signal activity representative of movement disorders based on a predetermined template developed for the patient.

5. The implantable medical device system of claim 1 wherein the implantable medical device is further configured with at least one analysis tool configured to derive the EEG parameters, and the software operating program and associated hardware of the external component is further configured to at least one of process, store, playback and display on the display of the external component the neurological event detected in the EEG signals based on the derived EEG parameters.

6. The implantable medical device system of claim 1 wherein the implantable medical device is further configured with operational parameters stored in the memory of the implantable medical device, and the software operating program and associated hardware of the external component is further configured to at least one of process, store, playback and display the operational parameters on the display of the external component.

7. The implantable medical device system of claim 1 wherein the display of EEG parameters on the external component may be directly associated with the display of the representation of the EEG signals.

8. The implantable medical device system of claim 1 wherein the display of EEG parameters on the display of the external component may be indirectly associated with the display of the representation of the EEG signals.

9. The implantable medical device system of claim 1, the implantable medical device further configured with:
    a therapy subsystem provided with at least one of a therapeutic stimulator, a sensory stimulator, and a diagnostic stimulator, wherein each of the therapeutic stimulator, the sensory stimulator and the diagnostic stimulator is configured to deliver a form of neuromodulation to the neural tissue of a patient, the form of neuromodulation characterized by one or more therapy parameters;
    a memory subsystem including the memory in which the representation of the EEG signals and the EEG parameters are stored and other memory in which the therapy parameters, if any, are stored, and
    the software operating program and associated hardware of the external component is further configured to at least one of process, store, playback and display on the display of the external component at least the representation of the EEG signals, the neurological event detected in the EEG signals based on the derived EEG parameters, if any, and the form of neuromodulation delivered, if any, based on the therapy parameters.

10. The implantable medical device system of claim 9, further comprising an adaptive subsystem configured to do one of the following based on the EEG parameters, if any: correlate or decorrelate the form of neuromodulation therapy based on one or more of the derived parameters.

11. The implantable medical device system of claim 1, wherein the external component is further configured to process the EEG parameters to derive a characteristic of the EEG signals.

12. The implantable medical device system of claim 11, wherein the EEG parameter comprises half-wave measurements and the derived characteristic is frequency content information.

13. The implantable medical device system of claim 11, wherein the EEG parameter comprises line length measurements and the derived characteristic is signal variation information.

14. The implantable medical device system of claim 11, wherein the EEG parameter comprises area measurements and the derived characteristic is energy information.

15. A method of communicating information between an implantable neurostimulator and at least one external component configured to process, store, playback and display on a display of the external component a representation of EEG signals acquired and stored in the implantable neurostimulator, comprising:

acquiring signal activity from the patient's brain from at least one sensor, the at least one sensor in operable communication with the implantable neurostimulator;

processing the signal activity with the implantable neurostimulator to provide a digital representation of the signal activity, and to detect a neurological event of interest based on one or more signal parameters derived from the signal activity;

storing the digital representation of the signal activity, together with the one or more signal parameters, in an area of memory in a memory subsystem of the implantable neurostimulator;

establishing a communication link between the implantable neurostimulator and the external component and communicating through the communication link the digital representation of the signal activity from the area of memory to the external component; and with a software operating program and associated hardware of the external component, processing and displaying on a display of the external component the representation of the signal activity and the signal parameters received from the implantable medical device, and processing the signal activity in order to simulate the detection of the neurological event.

* * * * *